(12) United States Patent
Ortiz et al.

(10) Patent No.: US 8,231,570 B2
(45) Date of Patent: Jul. 31, 2012

(54) INVERTED CONICAL EXPANDABLE RETRACTOR

(75) Inventors: Mark S. Ortiz, Milford, OH (US); Brandon L. Livingston, Mason, OH (US); Dhananjay V. Patil, Mumbai (IN); Frederick E. Shelton, IV, Hillsboro, OH (US); Jerome R. Morgan, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 264 days.

(21) Appl. No.: 12/636,020

(22) Filed: Dec. 11, 2009

(65) Prior Publication Data

US 2011/0144589 A1 Jun. 16, 2011

(51) Int. Cl.
*A61M 29/00* (2006.01)

(52) U.S. Cl. ............ 604/104; 604/364; 604/164.03

(58) Field of Classification Search ............ 604/164.02, 604/164.03, 167.07, 104, 256, 264
See application file for complete search history.

(56) References Cited

U.S. PATENT DOCUMENTS

| 3,397,699 | A | * | 8/1968 | Kohl ............................ 604/105 |
| 4,022,191 | A | | 5/1977 | Jamshidi |
| 4,608,977 | A | | 9/1986 | Brown |
| 4,809,694 | A | | 3/1989 | Ferrara |
| 5,031,634 | A | | 7/1991 | Simon |
| 5,053,042 | A | | 10/1991 | Bidwell |
| 5,100,387 | A | | 3/1992 | Ng |
| 5,122,122 | A | * | 6/1992 | Allgood ........................ 604/174 |
| 5,197,971 | A | * | 3/1993 | Bonutti ......................... 606/192 |
| 5,201,742 | A | | 4/1993 | Hasson |
| 5,235,987 | A | | 8/1993 | Wolfe |
| 5,312,417 | A | | 5/1994 | Wilk |
| 5,316,014 | A | | 5/1994 | Livingston |
| 5,320,111 | A | | 6/1994 | Livingston |
| 5,330,437 | A | | 7/1994 | Durman |
| 5,342,315 | A | | 8/1994 | Rowe et al. |
| 5,431,676 | A | | 7/1995 | Dubrul et al. |
| 5,494,039 | A | | 2/1996 | Onik et al. |
| 5,569,205 | A | | 10/1996 | Hart et al. |
| 5,628,732 | A | | 5/1997 | Antoon, Jr. et al. |
| 5,647,373 | A | | 7/1997 | Paltieli et al. |
| 5,707,359 | A | | 1/1998 | Bufalini |
| 5,857,999 | A | | 1/1999 | Quick et al. |

(Continued)

FOREIGN PATENT DOCUMENTS

EP 577400 A1 1/1994

(Continued)

OTHER PUBLICATIONS

International Search Report, PCT/US10/059627, Jul. 13, 2011.

(Continued)

*Primary Examiner* — Laura Bouchelle
(74) *Attorney, Agent, or Firm* — Nutter McClennen & Fish LLP

(57) ABSTRACT

Access devices and related methods are disclosed that generally involve flexible or adjustable cannulas that have a substantially cylindrical insertion configuration and a substantially conical expanded configuration. Various methods and features are provided for transitioning the cannula from the insertion configuration to the expanded configuration while the access device is inserted through tissue to form a conical opening through the tissue. Examples include cables, biasing elements, retaining elements, bimodal rings, and coil springs. The devices and methods disclosed herein can allow for improved retention of the access device, improved angulation of instruments passed through the access device, and can increase the integrity of a seal formed between the access device and surrounding tissue.

15 Claims, 19 Drawing Sheets

U.S. PATENT DOCUMENTS

| | | |
|---|---|---|
| 5,868,673 A | 2/1999 | Vesely |
| 5,882,340 A | 3/1999 | Yoon |
| 5,911,707 A | 6/1999 | Wolvek et al. |
| 5,916,175 A | 6/1999 | Bauer et al. |
| 5,941,889 A | 8/1999 | Cermak |
| 5,954,670 A | 9/1999 | Baker |
| 5,984,930 A | 11/1999 | Maciunas et al. |
| 6,017,356 A | 1/2000 | Frederick et al. |
| 6,033,426 A | 3/2000 | Kaji |
| D422,706 S | 4/2000 | Bucholz et al. |
| 6,048,321 A | 4/2000 | McPherson et al. |
| 6,110,182 A | 8/2000 | Mowlai-Ashtiani |
| 6,162,196 A | 12/2000 | Hart et al. |
| 6,195,577 B1 | 2/2001 | Truwit et al. |
| 6,203,499 B1 | 3/2001 | Imling |
| 6,216,029 B1 | 4/2001 | Paltieli et al. |
| 6,231,565 B1 | 5/2001 | Tovey et al. |
| 6,231,585 B1 | 5/2001 | Takahashi et al. |
| 6,236,875 B1 | 5/2001 | Bucholz et al. |
| 6,245,028 B1 | 6/2001 | Furst et al. |
| 6,283,942 B1 | 9/2001 | Staehlin et al. |
| 6,361,499 B1 | 3/2002 | Bates et al. |
| 6,379,307 B1 | 4/2002 | Filly et al. |
| 6,400,979 B1 | 6/2002 | Stoianovici et al. |
| 6,432,085 B1 | 8/2002 | Stellon et al. |
| 6,443,960 B1 | 9/2002 | Brabrand et al. |
| 6,445,943 B1 | 9/2002 | Ferre et al. |
| 6,468,226 B1 | 10/2002 | McIntyre, IV |
| 6,475,152 B1 | 11/2002 | Kelly, Jr. et al. |
| 6,490,467 B1 | 12/2002 | Bucholz et al. |
| 6,501,981 B1 | 12/2002 | Schweikard et al. |
| 6,529,765 B1 | 3/2003 | Franck et al. |
| 6,535,756 B1 | 3/2003 | Ruch et al. |
| 6,539,121 B1 | 3/2003 | Haskell et al. |
| 6,546,279 B1 | 4/2003 | Bova et al. |
| 6,547,782 B1 | 4/2003 | Charles et al. |
| 6,551,270 B1 | 4/2003 | Bimbo et al. |
| 6,665,554 B1 | 12/2003 | Charles et al. |
| 6,687,531 B1 | 2/2004 | Ferre et al. |
| 6,723,106 B1 | 4/2004 | Charles et al. |
| 6,731,966 B1 | 5/2004 | Spigelman et al. |
| 6,752,812 B1 | 6/2004 | Truwit |
| 6,770,027 B2 | 8/2004 | Banik et al. |
| 6,782,288 B2 | 8/2004 | Truwit |
| 6,783,524 B2 | 8/2004 | Anderson et al. |
| 6,785,572 B2 | 8/2004 | Yanof et al. |
| 6,808,492 B2 | 10/2004 | Snyder |
| 7,021,173 B2 | 4/2006 | Stoianovici et al. |
| 7,056,329 B2 | 6/2006 | Kerr |
| 7,076,106 B2 | 7/2006 | Haskell et al. |
| 7,083,626 B2 | 8/2006 | Hart et al. |
| 7,163,525 B2 | 1/2007 | Franer |
| 7,371,227 B2 | 5/2008 | Zeiner |
| 2003/0100814 A1 | 5/2003 | Kindlein |
| 2003/0208207 A1 | 11/2003 | Layer |
| 2003/0229338 A1 | 12/2003 | Irion et al. |
| 2004/0082969 A1 | 4/2004 | Kerr |
| 2004/0185453 A1 | 9/2004 | Myerson et al. |
| 2004/0230161 A1 | 11/2004 | Zeiner |
| 2004/0254426 A1 | 12/2004 | Wenchell |
| 2005/0222582 A1 | 10/2005 | Wenchell |
| 2006/0149137 A1 | 7/2006 | Pingleton et al. |
| 2006/0247499 A1 | 11/2006 | Butler et al. |
| 2006/0247673 A1 | 11/2006 | Voegele et al. |
| 2006/0276821 A1 | 12/2006 | Davison et al. |
| 2007/0185453 A1 | 8/2007 | Michael et al. |
| 2007/0260121 A1 | 11/2007 | Bakos et al. |
| 2007/0260273 A1 | 11/2007 | Cropper et al. |
| 2008/0086080 A1 | 4/2008 | Mastri et al. |
| 2008/0086167 A1 | 4/2008 | Mastri et al. |
| 2008/0249373 A1 | 10/2008 | Wenchell |
| 2008/0255519 A1 | 10/2008 | Piskun et al. |
| 2009/0005799 A1 | 1/2009 | Franer et al. |
| 2009/0105659 A1 | 4/2009 | Bettuchi et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0118830 A1 | 5/2010 | Stephenson et al. |
| 2010/0228091 A1 | 9/2010 | Widenhouse et al. |
| 2010/0228092 A1 | 9/2010 | Ortiz et al. |
| 2010/0228096 A1 | 9/2010 | Weisenburgh, II et al. |
| 2010/0261974 A1 | 10/2010 | Shelton, IV et al. |
| 2010/0268162 A1 | 10/2010 | Shelton, IV et al. |
| 2010/0312060 A1 | 12/2010 | Widenhouse et al. |
| 2010/0312061 A1 | 12/2010 | Hess et al. |
| 2010/0312063 A1 | 12/2010 | Hess et al. |
| 2010/0312064 A1 | 12/2010 | Weisenburgh, II et al. |
| 2010/0312189 A1 | 12/2010 | Shelton, IV et al. |
| 2011/0028793 A1 | 2/2011 | Martin et al. |
| 2011/0028794 A1 | 2/2011 | Widenhouse et al. |
| 2011/0124967 A1 | 5/2011 | Morgan et al. |
| 2011/0144437 A1 | 6/2011 | Ortiz et al. |
| 2011/0144440 A1 | 6/2011 | Cropper et al. |
| 2011/0144442 A1 | 6/2011 | Farrell et al. |
| 2011/0144443 A1 | 6/2011 | Shelton, IV et al. |
| 2011/0144444 A1 | 6/2011 | Sakai, Jr. et al. |
| 2011/0144447 A1 | 6/2011 | Schleitweiler et al. |
| 2011/0144448 A1 | 6/2011 | Shelton, IV et al. |
| 2011/0144449 A1 | 6/2011 | Ortiz et al. |
| 2011/0144590 A1 | 6/2011 | Sakai, Jr. et al. |

FOREIGN PATENT DOCUMENTS

| | | |
|---|---|---|
| WO | 9636283 A1 | 11/1996 |
| WO | 0041759 A1 | 7/2000 |
| WO | 0062689 A1 | 10/2000 |
| WO | 0108563 A2 | 2/2001 |
| WO | 2005097019 A2 | 10/2005 |
| WO | 2005097234 A2 | 10/2005 |
| WO | 2006057982 A2 | 6/2006 |

OTHER PUBLICATIONS

U.S. Appl. No. 12/339,473, filed Mar. 6, 2009, Methods and Devices for Providing Access Into a Body Cavity.

U.S. Appl. No. 12/399,482, filed Mar. 6, 2009, Methods and Devices for Providing Access Into a Body Cavity.

U.S. Appl. No. 12/399,547, filed Mar. 6, 2009, Surgical Access Devices and Methods Providing Seal Movement in Predefined Paths.

U.S. Appl. No. 12/399,625, filed Mar. 6, 2009, Methods and Devices for Providing Access Into a Body Cavity.

U.S. Appl. No. 12/420,146, filed Apr. 8, 2009, Methods and Devices for Providing Access Into a Body Cavity.

U.S. Appl. No. 12/424,213, filed Apr. 15, 2009, Cannula With Sealing Elements.

U.S. Appl. No. 12/478,862, filed Jun. 15, 2009, Flexible Cannula Devices and Methods.

U.S. Appl. No. 12/478,882, filed Jun. 15, 2009, Multi-Planar Obturator With Foldable Retractor.

U.S. Appl. No. 12/479,030, filed Jun. 5, 2009, Retractor With Integrated Wound Closure.

U.S. Appl. No. 12/479,096, filed Jun. 5, 2009, Interlocking Seal Components.

U.S. Appl. No. 12/479,293, filed Jun. 5, 2009, Methods and Devices for Providing Access Through Tissue to Surgical Site.

U.S. Appl. No. 12/479,395, filed Jun. 5, 2009, Methods and Devices for Accessing a Body Cavity Using Surgical Access Device With Modular Seal Components.

U.S. Appl. No. 12/512,542, filed Jul. 30, 2009, Methods and Devices for Providing Access Into a Body Cavity.

U.S. Appl. No. 12/512,568, filed Jun. 30, 2009, Methods and Devices for Providing Access Into a Body Cavity.

U.S. Appl. No. 12/636,184, filed Dec. 11, 2009, Methods and Devices for Providing Access Through Tissue to a Surgical Site.

U.S. Appl. No. 12/636,191, filed Dec. 11, 2009, Methods and Devices for Providing Access Through Tissue to a Surgical Site.

U.S. Appl. No. 12/636,205, filed Dec. 11, 2009, Methods and Devices for Providing Access Through Tissue to a Surgical Site.

U.S. Appl. No. 12/636,232, filed Dec. 11, 2009, Methods and Devices for Providing Access Through Tissue to a Surgical Site.

U.S. Appl. No. 12/635,754, filed Dec. 11, 2009, Methods and Devices for Providing Access Into a Body Cavity.

U.S. Appl. No. 12/635,762, filed Dec. 11, 2009, Methods and Devices for Providing Access Into a Body Cavity.

U.S. Appl. No. 12/635,990, filed Dec. 11, 2009, Methods and Devices for Accessing a Body Cavity.

U.S. Appl. No. 12/623,018, filed Nov. 20, 2009, Discrete Flexion Head for Single Port Device.

U.S. Appl. No. 12/636,174, filed Dec. 11, 2009, Methods and Devices for Providing Access Through Tissue to a Surgical Site.

* cited by examiner

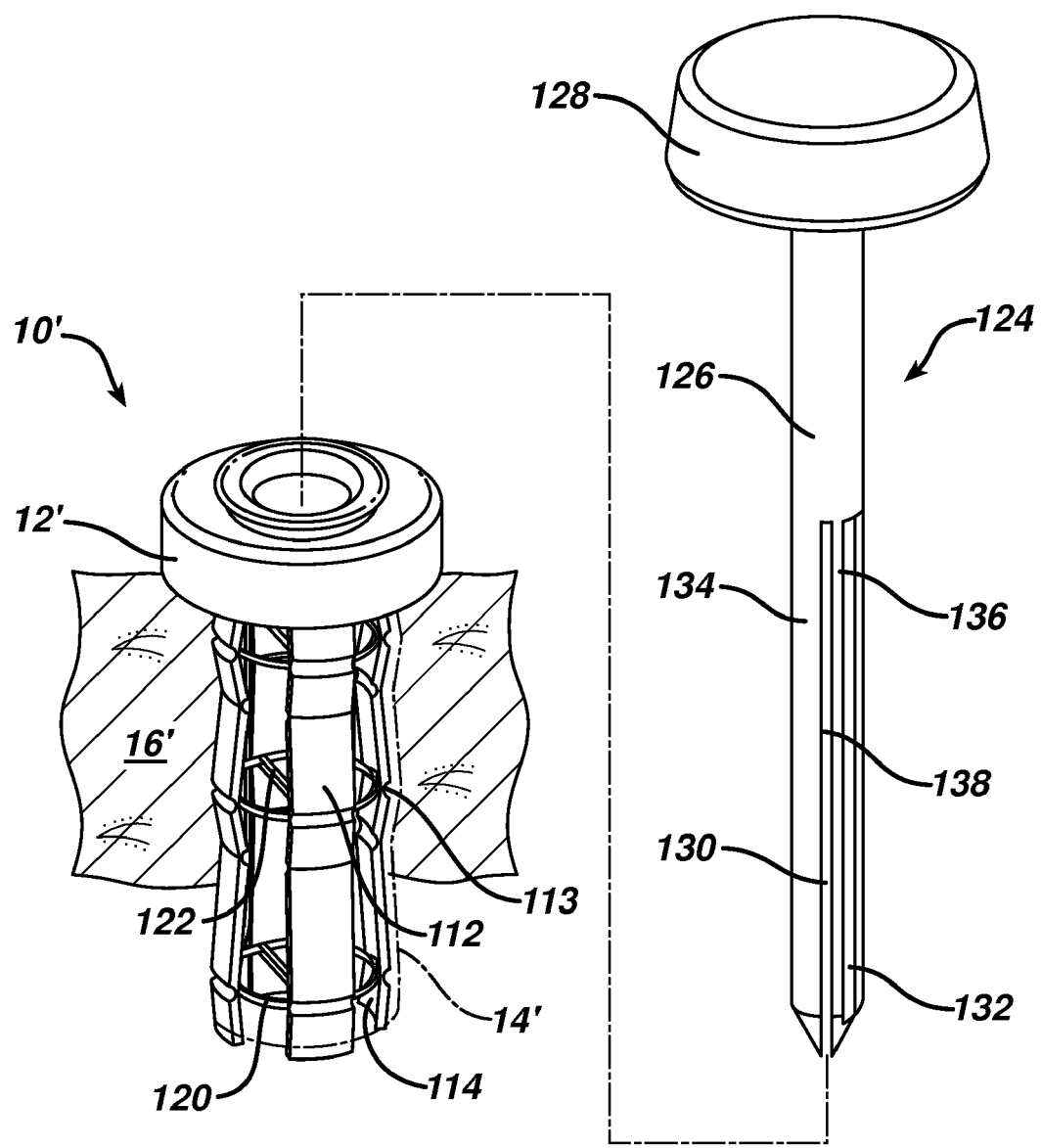

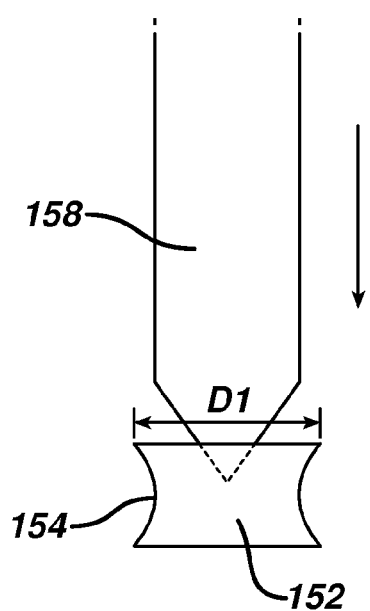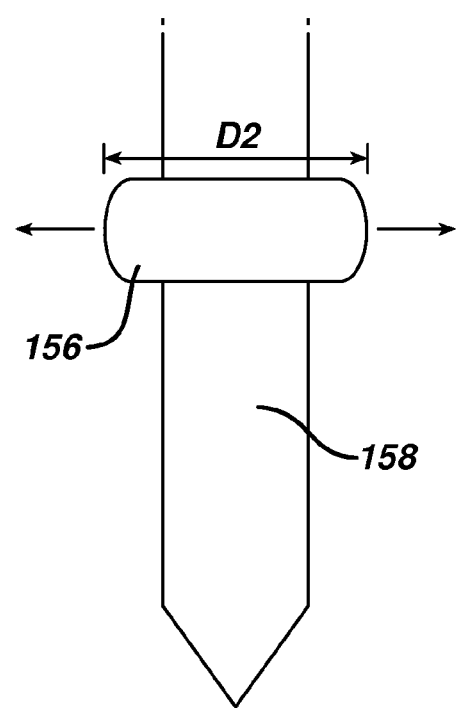
FIG. 8A
FIG. 8B

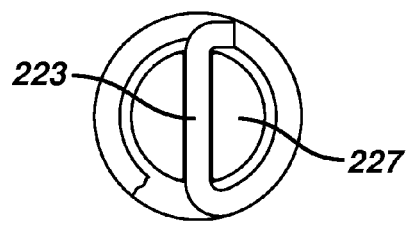
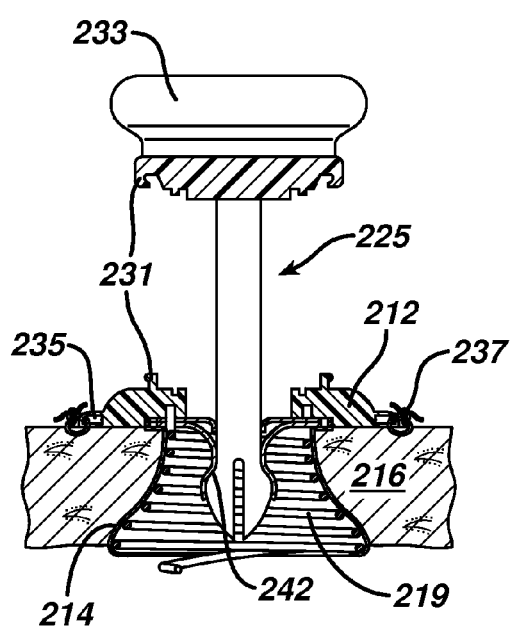
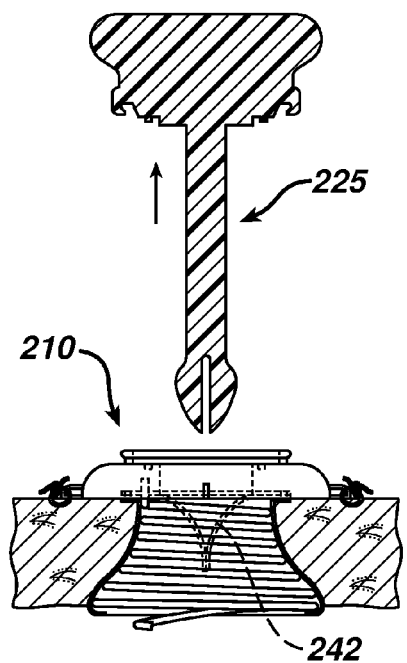

INVERTED CONICAL EXPANDABLE RETRACTOR

CROSS REFERENCE TO RELATED APPLICATIONS

The present application is being filed concurrently with PreGrant Publication No. 2011/0144443 entitled "INVERTED CONICAL EXPANDABLE RETRACTOR WITH COIL SPRING" which is incorporated by reference herein in its entirety.

FIELD OF THE INVENTION

The present invention relates to methods and devices for performing surgical procedures, and in particular to methods and devices for accessing a body cavity.

BACKGROUND OF THE INVENTION

In many surgical procedures, it is desirable to provide one or more working channels into a body cavity through which various instruments can be passed to view, engage, and/or treat tissue to achieve a diagnostic or therapeutic effect. In laparoscopic abdominal procedures for example, the abdominal cavity is generally insufflated with $CO_2$ gas to a pressure of around 15 mm Hg. The abdominal wall is pierced and one or more tubular cannulas, each defining a working channel, are inserted into the abdominal cavity. A laparoscopic telescope connected to an operating room monitor can be used to visualize the operative field and can be placed through one of the working channels. Other laparoscopic instruments such as graspers, dissectors, scissors, retractors, etc. can also be placed through one or more of the working channels to facilitate various manipulations by the surgeon and/or surgical assistant(s).

One problem with existing methods and devices is that these tubular cannulas limit the degree to which devices passed through the cannula can be angulated with respect to the operative field. This can undesirably prolong and complicate the surgery, and in same cases can require placement of additional access devices and formation of additional incisions associated therewith.

Another drawback to existing access devices is that they can suffer from poor retention and sealing capabilities. For example, angulation of various surgical tools inserted through traditional cannulas can compromise the seal between the cannula and the tissue wall, undesirably allowing insufflation gas to escape. In addition, the cannula can have a tendency to "back out" or slide proximally out of the incision.

Accordingly, there is a need for surgical access methods and devices that provide improved sealing, retention, and maneuverability characteristics.

SUMMARY OF THE INVENTION

The access devices and methods disclosed herein generally involve flexible or adjustable cannulas that have a substantially cylindrical insertion configuration and a substantially conical expanded configuration. Various methods and features are provided for transitioning the cannula from the insertion configuration to the expanded configuration when the access device is inserted through tissue to form a conical opening through the tissue. Examples include cables, biasing elements, retaining elements, bimodal rings, and/or coil springs. The devices and methods disclosed herein can allow for improved retention of the access device, improved angulation of instruments passed through the access device, and can increase the integrity of a seal formed between the access device and surrounding tissue.

In one exemplary embodiment, an adjustable access device is provided. The access device can include a housing having a cannula extending distally therefrom. The housing and the cannula can define a working channel extending therethrough for receiving instruments and the access device can include at least one seal element disposed within the working channel and configured to form a seal around an instrument disposed through the working channel and/or a seal across the working channel when no instrument is disposed therethrough. The cannula can have an insertion configuration with a substantially constant outer diameter between a proximal end and a distal end, and an expanded configuration wherein the diameter increases from the proximal end of the cannula to the distal end of the cannula. The cannula can be folded in the expanded configuration and unfolded in the insertion configuration.

In one embodiment, the cannula can include a flexible outer sheath having a plurality of folding walls disposed therein, each folding wall comprising a plurality of segments. The plurality of segments can include a plurality of long segments separated from each other by at least one short segment, and the segments can be defined by a plurality of livings hinges formed in the folding walls. In one embodiment, the living hinges alternate between being formed in an interior surface of the folding walls and being formed in an exterior surface of the folding walls. The plurality of long segments can have progressively increasing lengths from the proximal end of the folding walls to the distal end of the folding walls and each of the short segments can have lengths less than the long segments and substantially the same length as one another.

In another exemplary embodiment, the access device can include an actuator coupled between the housing and the cannula and configured to move the cannula between the insertion configuration and the expanded configuration. For example, the actuator can comprise at least one cable extending distally from the housing to the distal end of the cannula. The housing can include a rotatable member coupled to the at least one cable and configured to rotate to selectively tension the at least one cable.

In another embodiment, the access device can include at least one biasing element disposed within the cannula and configured to bias the cannula towards the expanded configuration. The access device can also include a horizontal retaining element coupled to the biasing element such that the cannula is maintained in the insertion configuration and/or a vertical retaining element coupled to the biasing element such that the cannula is maintained in the expanded configuration.

In yet another exemplary embodiment, an adjustable access device is provided that can include a cannula defining a working channel extending therethrough for receiving instruments, the cannula having an insertion configuration with a substantially constant outer diameter between a proximal end and a distal end, and an expanded configuration wherein the outer diameter increases from the proximal end of the cannula to the distal end of the cannula. The access device can also include a plurality of springs disposed circumferentially around the cannula, the springs being biased such that they apply an inward force to the cannula to bias the cannula to the expanded configuration. The cannula can be configured such that insertion of an obturator into the cannula is effective to radially expand the plurality of springs to move the cannula to the insertion configuration and removal of the obturator from the working channel allows the springs to decrease in diameter to move the cannula to the expanded configuration. The access device can also include an obturator insertable through the working channel of the cannula that is effective, when inserted, to radially expand the plurality of springs such that the cannula is shifted to the insertion configuration.

In one embodiment, the cannula can comprise a flexible outer sheath having a plurality of folding walls disposed therein, each folding wall comprising a plurality of long segments separated from each other by at least one short segment, wherein the segments are defined by a plurality of living hinges formed in the folding walls.

In yet another embodiment, a method for accessing a surgical site is provided that includes inserting a cannula through a tissue wall and folding a plurality of folding walls of the cannula to form a conical shaped opening through the tissue wall. Folding the plurality of folding walls can further include inserting an obturator through the cannula to sever at least one retaining element and allow at least one spring to expand radially and/or applying tension to at least one cable coupled to the distal end of the cannula. Folding the plurality of folding walls can also include removing an obturator from the cannula to allow a plurality of springs to contract radially against an outer surface of the cannula.

In another embodiment, an adjustable access device is provided that can include a housing and an expandable cannula extending distally from the housing, the expandable cannula including a coil spring having a proximal end coupled to the housing and a distal end configured to rotate relative to the housing to adjust a diameter of the cannula such that the coil spring is effective to move the expandable cannula between an insertion configuration, in which the cannula has a substantially constant outer diameter between a proximal end and a distal end, and an expanded configuration, in which the diameter of the cannula increases from the proximal end of the cannula to the distal end of the cannula. The access device can also include at least one seal element disposed within a working channel extending through the housing and the cannula, the at least one seal element being configured to form a seal around an instrument disposed through the working channel and/or a seal across the working channel when no instrument is disposed therethrough. The cannula can include at least one sheath disposed around the coil spring and the distal end of the coil spring can extend at least partially across a longitudinal axis of the cannula.

In one embodiment, the coil spring can have a plurality of coils extending radially around a longitudinal axis of the cannula, the spring being biased to an expanded configuration in which a distal coil of the spring has a diameter greater than a diameter of a proximal coil of the spring such that the spring defines a conical opening extending therethrough.

In another embodiment, the access device can include an obturator having a distal end configured to engage the distal end of the coil spring such that rotation of the obturator is effective to rotate the distal end of the coil spring relative to the housing. The distal end of the obturator can include a longitudinally-extending slot formed therein for receiving and engaging the distal end of the coil spring. The obturator can also include a mating element formed on a proximal portion thereof, the mating element being configured to engage the housing to prevent rotation of the obturator with respect to the housing. In one embodiment, the housing can include one or more suture anchors to facilitate securing the housing to a tissue.

In yet another embodiment, a method for accessing a surgical site is provided that includes inserting a cannula of a surgical access device through a tissue wall and releasing a coil spring disposed within the cannula such that the coil spring radially expands to cause the cannula to radially expand into a conical configuration thereby forming a conical opening through the tissue wall. Releasing the coil spring can include releasing a distal end of the coil spring such that the distal end of the coil spring rotates relative to a proximal end of the coil spring and relative to a housing coupled to the proximal end of the coil spring. In one embodiment, the distal end of the coil spring can be released from an obturator engaging the coil spring. Releasing the coil spring can also include detaching an obturator from a housing coupled to a proximal end of the cannula to release a distal end of the coil spring from a distal end of the obturator. In one embodiment, the method can include engaging a distal end of the coil spring and rotating the distal end of the coil spring relative to the housing to wind the coil spring and thereby move the cannula to an insertion configuration, in which an inner diameter of the cannula is substantially constant.

BRIEF DESCRIPTION OF THE DRAWINGS

The invention will be more fully understood from the following detailed description taken in conjunction with the accompanying drawings, in which:

FIG. 7A is a perspective view of another embodiment of an access device and an obturator configured to be inserted therethrough, the access device having a cannula in an insertion configuration;

FIG. 8A is a side view of one embodiment of bimodal ring and an obturator inserted partially therethrough;

FIG. 8B is a side view of the bimodal ring of FIG. 8A with the obturator inserted fully therethrough;

FIG. 10B is a bottom view of the coil spring and obturator of FIG. 10A;

FIG. 10C is a cross-sectional view of the access device of FIG. 10A, with the obturator partially removed therefrom and the cannula in an expanded configuration;

FIG. 10D is a cross-sectional view of the access device of FIG. 10A, with the obturator completely removed therefrom;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A person skilled in the art will appreciate that, while methods and devices are described herein in connection with minimally invasive laparoscopic procedures in the abdominal cavity, the methods and devices can be used in almost any part of a human or animal body and in various other types of surgical procedures. By way of non-limiting example, the devices and methods disclosed herein can be used in the thoracic cavity, pelvic cavity, cranial cavity and/or any of the body's natural orifices and can be used in endoscopic procedures and/or in open surgical procedures.

In general, surgical methods and access devices are provided that involve flexible or adjustable cannulas that have a substantially cylindrical insertion configuration and a substantially conical expanded configuration. Various features are provided for transitioning the cannula from the insertion configuration to the expanded configuration while it is inserted through tissue to form a conical opening through the tissue. Such devices and methods can allow for improved retention of the cannula, improved angulation of instruments passed through the cannula, and can increase the integrity of the seal between the cannula and the tissue wall.

Figure 1:
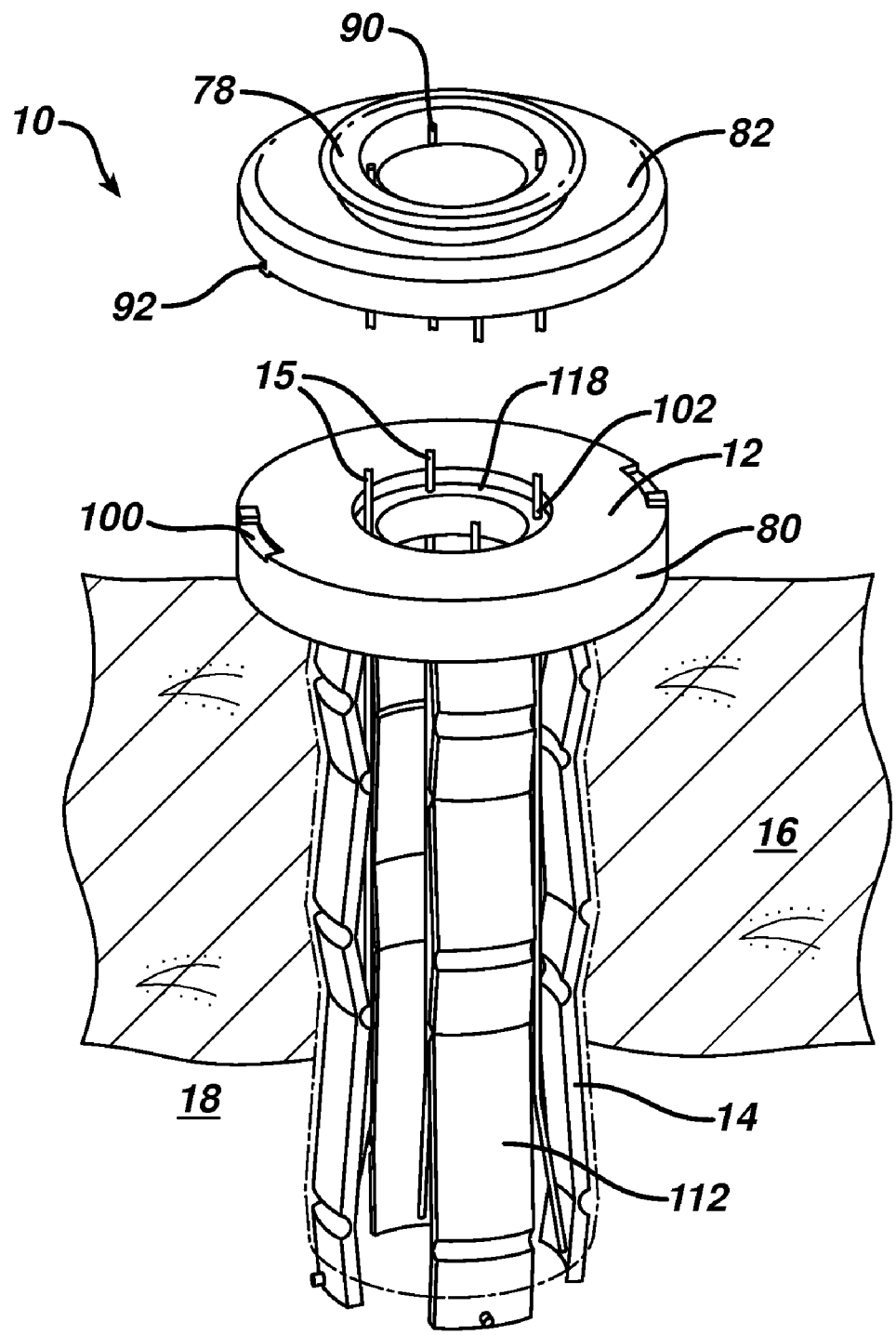
FIG. 1 is a partially-exploded perspective view of one embodiment of an access device inserted in a tissue wall and having a cannula in an insertion configuration.
Figure 2:
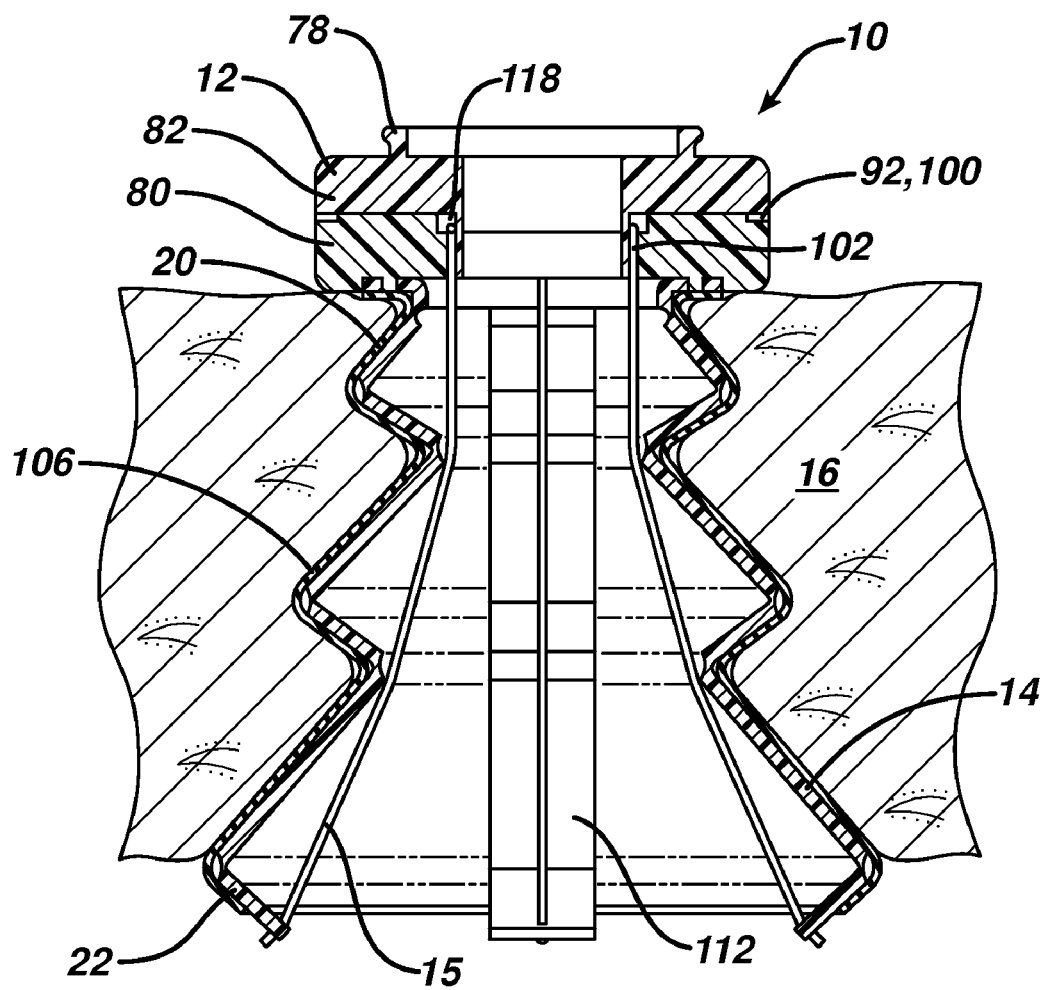
FIG. 2 is a cross-sectional view of the access device and tissue wall of FIG. 1, with the cannula shown in an expanded configuration.
Figure 3:
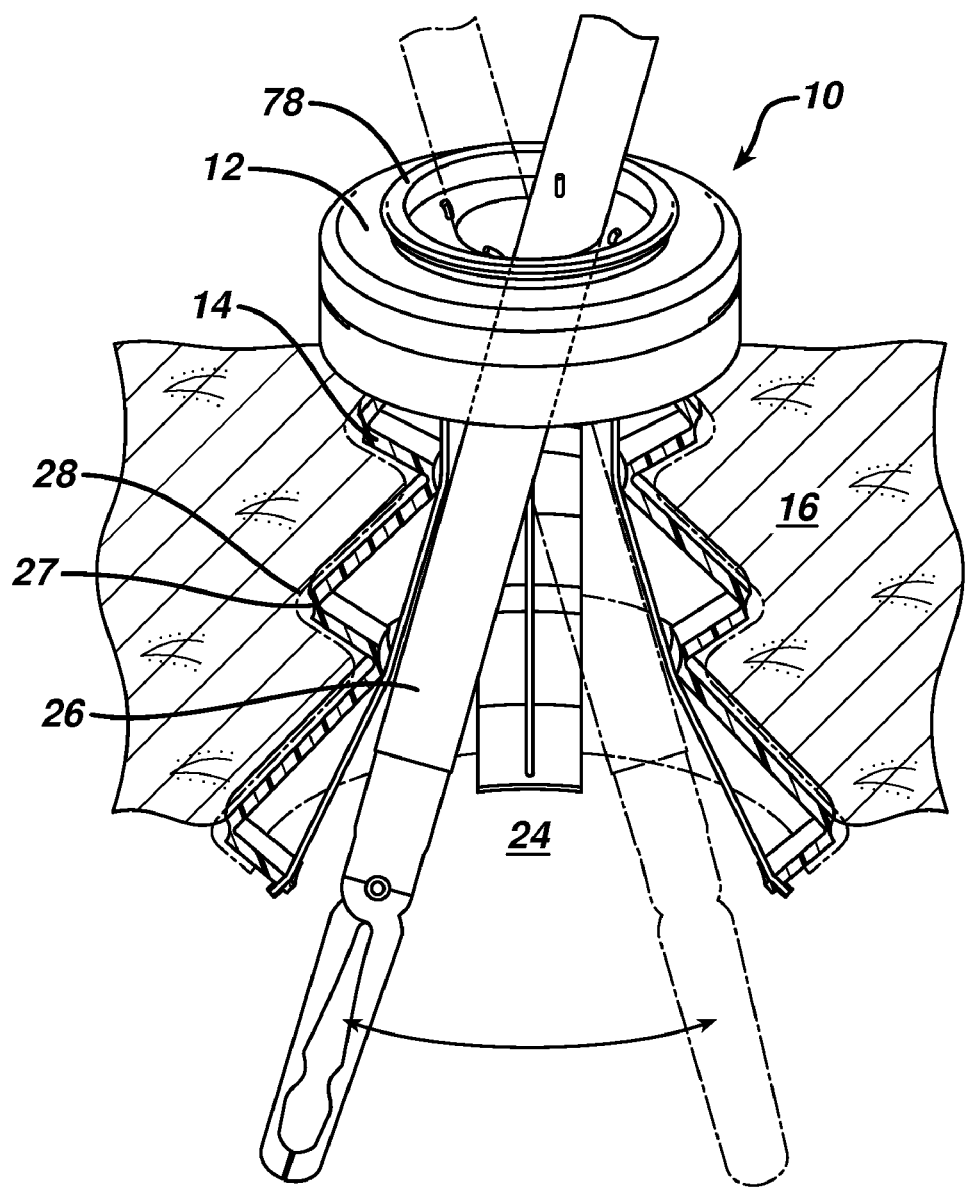
FIG. 3 is a cross-sectional view of the access device of FIGS. 1-2 with a surgical tool inserted therethrough.

FIG. 1 illustrates one exemplary embodiment of an access device 10. As shown, the access device 10 generally includes a housing 12 having a cannula 14 extending distally therefrom. The cannula 14 can be inserted through a tissue wall 16 while the cannula is in a substantially cylindrical insertion configuration with a substantially constant outer diameter to access a body cavity 18. As shown in FIG. 2, the cannula 14 can also have an expanded configuration in which the diameter of the cannula 14 increases from the proximal end 20 of the cannula to the distal end 22. In an exemplary embodiment, the cannula 14 is unfolded in the insertion configuration (FIG. 1) and is folded in the expanded configuration (FIG. 2). As discussed in detail below, an actuator can be provided to facilitate folding and unfolding the cannula 14. The actuator can have a variety of configurations, but in the illustrated embodiment, the actuator includes one or more cables 15. As shown in FIG. 3, the expanded cannula 14 can be effective to create a conical opening 24 through the tissue wall 16. The conical opening 24 can allow a surgical instrument 26 inserted through the housing 12 and cannula 14 to be angulated to a greater degree than traditional cylindrical openings. In addition, the conical opening 24 can increase the integrity of the seal between the outer surface 27 of the cannula 14 and the incision surface 28 and can provide increased resistance to proximal translation of the access device 10 with respect to the tissue wall 16.

Figure 4A:
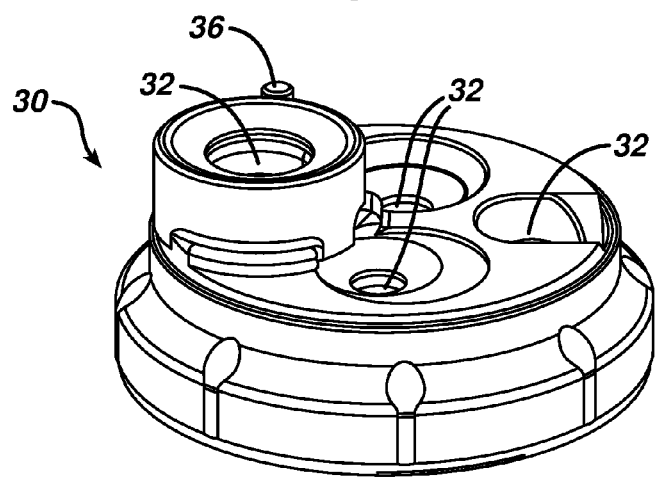
FIG. 4A is a perspective view of one embodiment of a seal housing.
Figure 4B:
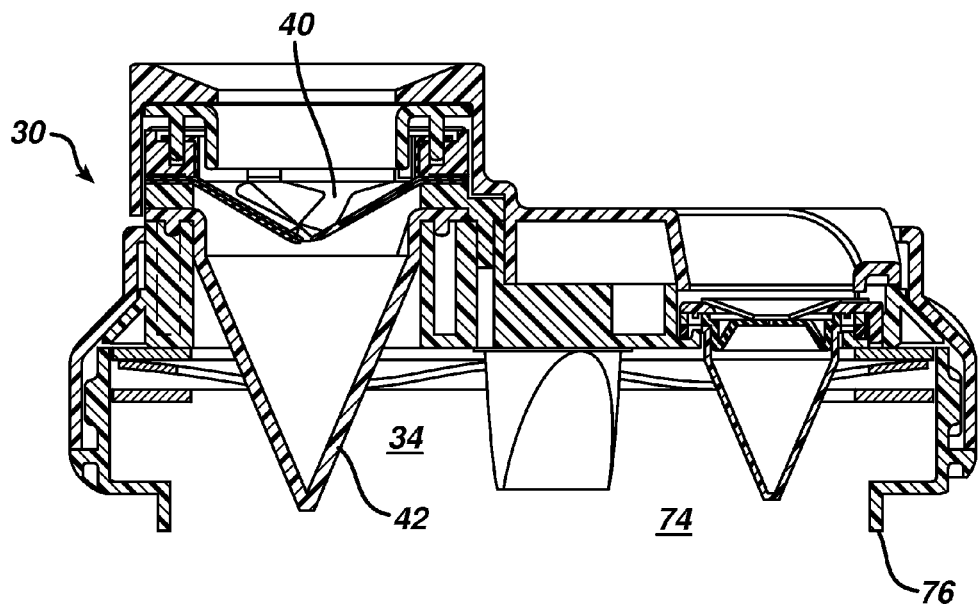
FIG. 4B is a cross-sectional view of the seal housing of FIG. 4A, showing one embodiment of an instrument seal and a zero-closure seal.

The access devices disclosed herein can include a seal housing that can be formed integrally with the housing or can be selectively attached thereto. A number of configurations are available for the seal housing. FIGS. 4A and 4B show one embodiment of a seal housing 30 having a generally cylindrical shape. One or more openings 32 can be formed in the proximal end of the seal housing 30 and the opening(s) can be coaxial or offset from an axis of a working channel 34 extending through the seal housing 30 and through the cannula 14. The seal housing 30 can also include other features, such as an insufflation port 36 for allowing and preventing the passage of an insufflation fluid, e.g. carbon dioxide, through the access device 10 and into a body cavity.

Typically, during surgical procedures in a body cavity such as the abdomen, insufflation fluid is provided through the access device 10 to expand the body cavity to facilitate the surgical procedure. In order to maintain insufflation within the body cavity, the seal housing 30, housing 12, and/or cannula 14 can include at least one seal disposed therein to prevent fluid from escaping. Various seal configurations are known in the art, but typically the access device includes an instrument seal that forms a seal around an instrument inserted therethrough, but otherwise does not form a seal when no instrument is inserted therethrough, a trocar seal or zero-closure seal that seals the working channel when no instrument is inserted therethrough, or a combination instrument seal and trocar seal that is effective to both form a seal around an instrument inserted therethrough and to form a seal in the working channel when no instrument is inserted therethrough. In the embodiment shown in FIGS. 4A and 4B, the seal housing 30 includes an instrument seal 40 and a separate trocar or zero-closure seal 42. A person skilled in the art will appreciate, however, that various other seals known in the art can be used, including for example, flapper valves, gel seals, diaphragm seals, etc.

Figure 4C:
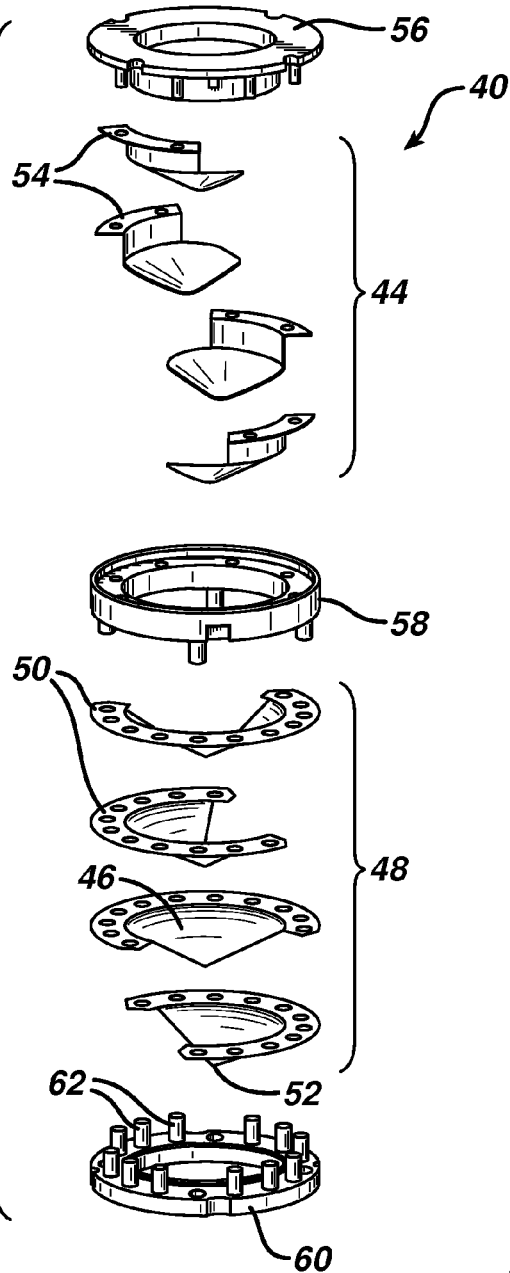
FIG. 4C is an exploded perspective view of the instrument seal of FIG. 4B.

The instrument seal 40 is shown in more detail in FIG. 4C. As shown, the instrument seal 40 is generally in the form of a multi-layer protective member 44 disposed on a proximal surface 46 of a multi-layer conical seal 48. The multi-layer conical seal 48 can include a series of overlapping seal segments 50 that are assembled in a woven arrangement to provide a complete seal body. The seal segments 50 can be stacked on top of one another or woven together in an overlapping fashion to form the multi-layer seal 48 having a central opening 52 therein. The seal segments 50 can be made from any number of materials known to those skilled in the art, but in an exemplary embodiment the seal segments 50 are formed from an elastomeric material. The seal segments 50 can also be molded such that they have a varying thickness across the profile of the seal 48. Varying the thickness across the profile of the seal 48 can be effective to minimize leakage and reduce drag forces on instruments passed therethrough. The multi-layer protective member 44 can similarly be formed from a series of overlapping segments 54 that are disposed proximal to the overlapping seal segments 50 and that are configured to protect the seal segments 50 from damage caused by surgical instruments inserted through the opening 52 in the seal 48. The protective member 44 can also be formed from various materials, but in certain exemplary embodiments the protective member 44 is formed from a molded thermoplastic elastomer. The segments 50, 54 that form the seal 48 and the protective member 44 can be held together using various techniques known in the art. As shown in FIG. 4C, the segments 50, 54 are held together by several ring members that mate to engage the segments 50, 54 therebetween. In particular, the protective member 44 is engaged between a crown 56 and a gasket ring 58, and the seal 48 is engaged between the gasket ring 58 and a retainer ring 60. Pins 62 are used to mate the ring members 56, 58, 60 and to extend through and engage the segments of the seal 48 and the protective member 44.

When fully assembled, the instrument seal 40 can be disposed at various locations within the access device 10. In the embodiment illustrated in FIGS. 4A and 4B, the instrument seal 40 is disposed in the seal housing 30 of the access device 10 at a location just distal of a proximal opening 32 and proximal of a trocar seal 42. Alternatively, or in addition, one or more seals can be positioned in the housing 12 and/or the cannula 14. In use, an instrument can be inserted into the center of the seal assembly and the seal segments 50, 54 can engage and form a seal around an outer surface of the instrument to thereby prevent the passage of fluids through the seal 40. When no instrument is inserted therethrough, the opening will not form a seal in the working channel 34, however other configurations in which a seal is formed when no instrument is inserted therethrough are also conceivable. Exemplary instrument seal configurations are described in more detail in U.S. Publication No. 2004/0230161 entitled "Trocar Seal Assembly," filed on Mar. 31, 2004, and U.S. Publication No. 2007/0185453 entitled "Conical Trocar Seal," filed on Oct. 15, 2003, which are hereby incorporated by reference in their entireties.

Figure 4D:
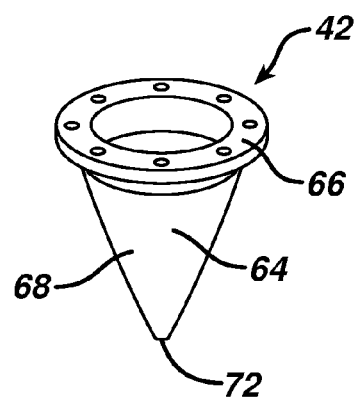
FIG. 4D is a perspective view of the zero-closure seal of FIG. 4B.

The trocar or zero-closure seal 42 in the illustrated embodiment is shown in more detail in FIG. 4D, and as shown, the illustrated zero-closure seal is in the form of a duckbill seal 64. The seal 64 is configured to form a seal in the working channel 34 when no instrument is inserted therethrough to thus prevent the leakage of insufflation gases delivered through the access device 10 to the body cavity. As shown, the duckbill seal 64 has a generally circular flange 66 with a sidewall 68 extending distally therefrom. The shape of the sidewall 68 can vary, but in the illustrated embodiment, the sidewall 68 is generally conical and extends in a distal direction to a seal face 72. The sidewall 68 is movable to allow the seal face 72 to move between a closed position, in which no instrument is inserted therethrough and the seal face 72 seals the working channel 34 of the access device 10, and an open position in which an instrument is inserted therethrough. The seal can include various other features, as described in more detail in U.S. Publication No. 2009/0005799 entitled "Duckbill Seal with Fluid Drainage Feature," filed on Jun. 29, 2007, which is hereby incorporated by reference in its entirety. A variety of other duckbill-type seals are known to those skilled in the art.

In accordance with the present disclosure the general structure of the seals as well as the seal housing do not generally form part of the present invention. As such, a person skilled in the art will appreciate that various seal configurations, as well as various seal housings or other access devices, can be used without departing from the spirit of the invention disclosed herein.

The seal housing 30 can have a distal opening 74 defined by a distal rim 76. The distal rim 76 can be configured to couple to a corresponding snap ring 78 formed on a proximal surface of the housing 12. The seal housing 30 can be formed integrally with the housing 12 or can be coupled thereto using a variety of means known in the art, including for example friction fittings, a snap fittings, clamps, screws, pins, magnets, electromagnets, etc.

Figure 5A:
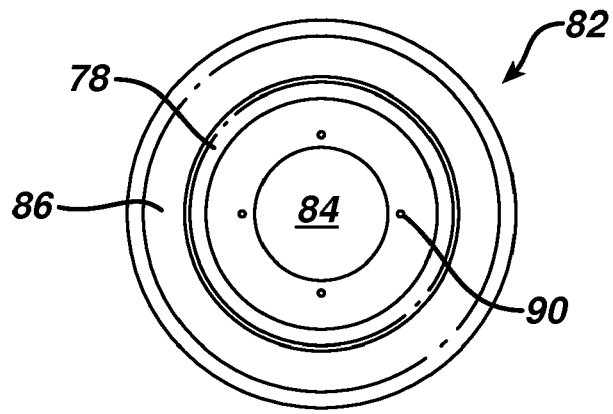
FIG. 5A is a top view of a housing top portion of the access device of FIGS. 1-2.
Figure 5B:
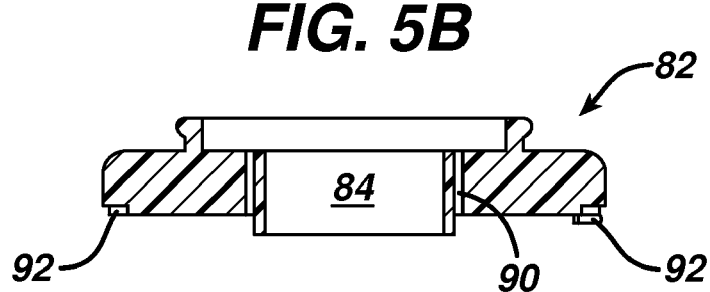
FIG. 5B is a cross-sectional side view of the housing top portion of FIG. 5A.
Figure 5C:
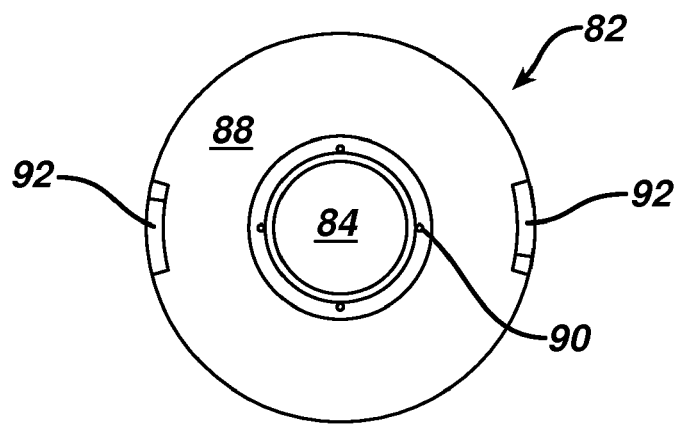
FIG. 5C is a bottom view of the housing top portion of FIG. 5A.

The housing 12 can have a variety of configurations. In the embodiment illustrated in FIGS. 1-3, the housing 12 is generally in the form of an annular disk. The housing has a distal base portion 80 and a proximal top portion 82. The top portion 82 is shown in more detail in FIGS. 5A-5C. As shown, the top portion 82 is in the form of an annular disk having a central opening 84, a proximal surface 86, and a distal surface 88. One or more apertures 90 are formed through the top portion 82 and are configured to receive the proximal ends of the cables 15 shown in FIGS. 1-3. Where multiple apertures 90 are provided, the apertures in an exemplary embodiment are spaced an equal distance apart from each other about the circumference of the central opening 84. The proximal surface 86 of the top portion 82 can include a snap ring 78 configured to couple the housing 12 to a seal housing 30 such that the working channel 34 of the seal housing 30 is substantially coaxial with the central opening 84 formed through the top portion 82. The distal surface 88 of the top portion 82 can include one or more rotation locks formed thereon or therein. In the illustrated embodiment, the rotation locks are in the form of a pair of L-shaped male tabs 92 extending distally from the distal surface 88.

Figure 5D:
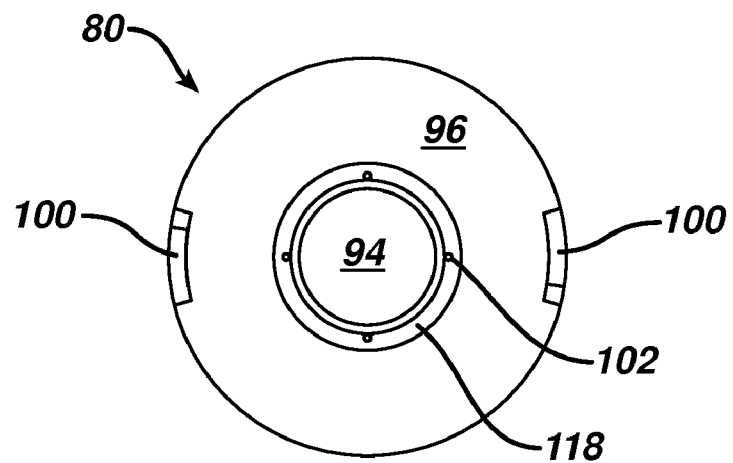
FIG. 5D is a top view of a housing base portion of the access device of FIGS. 1-2.
Figure 5E:
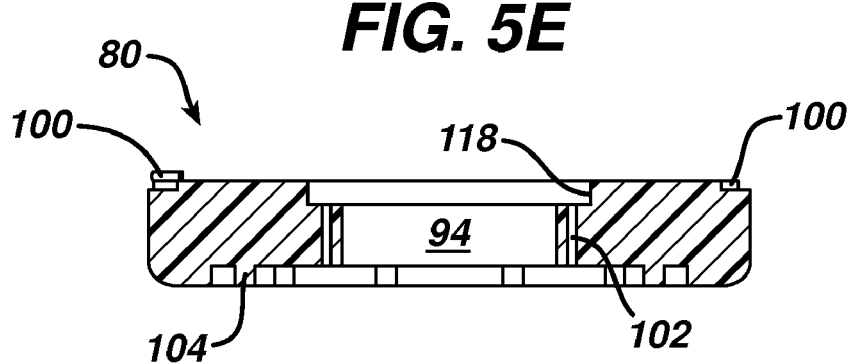
FIG. 5E is a cross-sectional side view of the housing base portion of FIG. 5D.
Figure 5F:
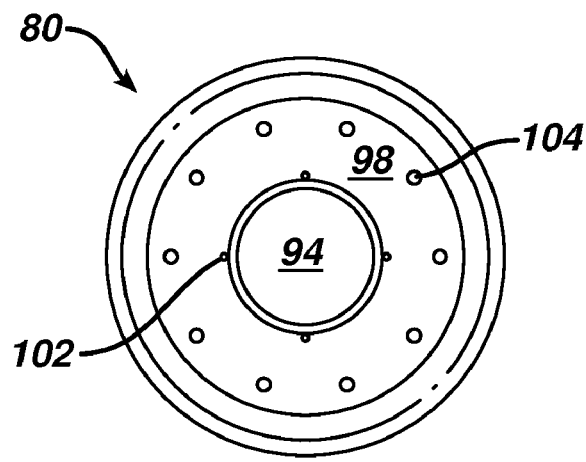
FIG. 5F is a bottom view of the housing base portion of FIG. 5D.

The base portion 80 of the housing 12 is shown in more detail in FIGS. 5D-5F. Like the top portion 82, the base portion 80 is generally in the form of an annular disk having a central opening 94, a proximal surface 96, and a distal surface 98. When assembled, the central opening 94 in the base portion 80 can be configured to be substantially coaxial with the central opening 84 in the top portion 82, the working channel 34 of the seal housing 30, and a working channel of the cannula 14 such that a continuous working channel exists through the entire length of the access device 10. The proximal surface 96 of the base portion 80 can include one or more rotation locks formed thereon or therein. In the illustrated embodiment, the rotation locks are in the form of a pair of L-shaped female slots 100 configured to receive the male tabs 92 formed on the distal surface 88 of the top portion 82. A person having ordinary skill in the art will appreciate that the tabs 92 and slots 100 can be swapped such that the top portion 82 includes the female slots and the base portion 80 includes the male tabs. A variety of other rotation locking mechanisms known in the art can also be employed to restrict rotation of the top portion 82 and the base portion 80 with respect to each other. One or more apertures 102 can be formed in the base portion 80 that are configured to slidably receive the cables 15 of FIGS. 1-3 therethrough, as will be explained in detail below. In addition, one or more pins 104 can be formed on the distal surface 98 of the base portion 80 to assist in mating the base portion 80 to the cannula 14.

Figure 6A:
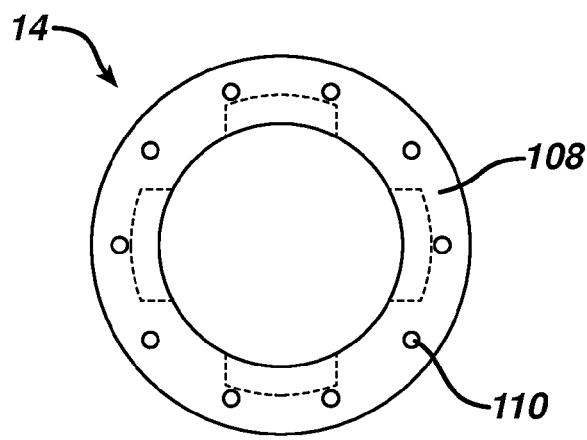
FIG. 6A is a top view of the cannula of FIGS. 1-2.
Figure 6B:
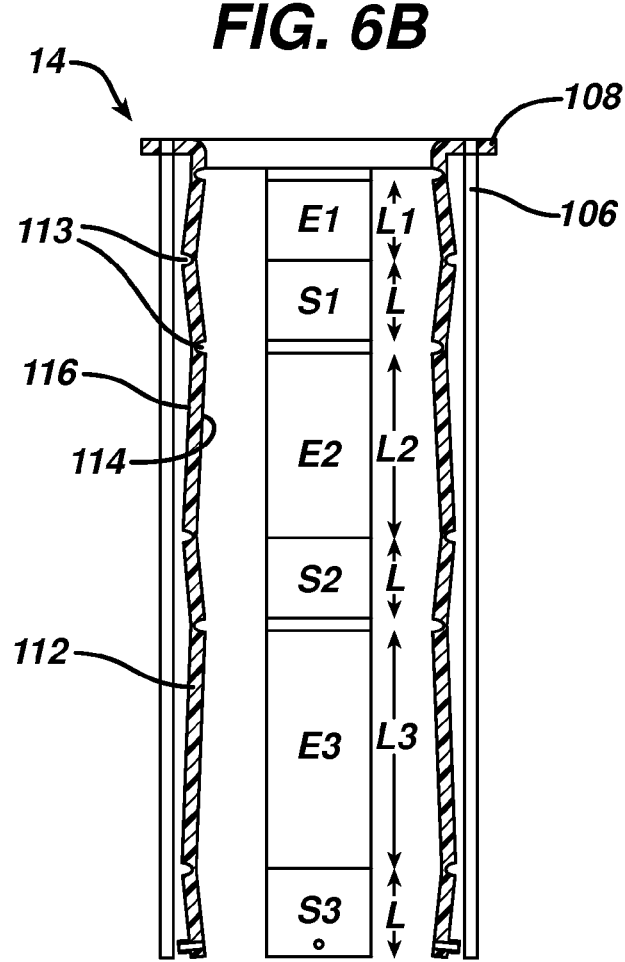
FIG. 6B is a side view of the cannula of FIG. 6A.

The cannula 14 can also have various shapes and configurations. In one embodiment, as shown in FIGS. 6A and 6B, the cannula 14 includes a flexible and/or stretchable sheath 106 extending distally from an annular flange 108. The annular flange 108 can have one or more apertures 110 formed therein for receiving the pins 104 formed on the distal surface 98 of the base portion 80 and for mating the cannula 14 to the housing 12. The cannula can further include one or more folding walls 112 extending distally from the flange 108. In the illustrated embodiment, four folding walls 112 are shown spaced approximately 90 degrees apart about the circumference of the annular flange 108.

Figure 6C:
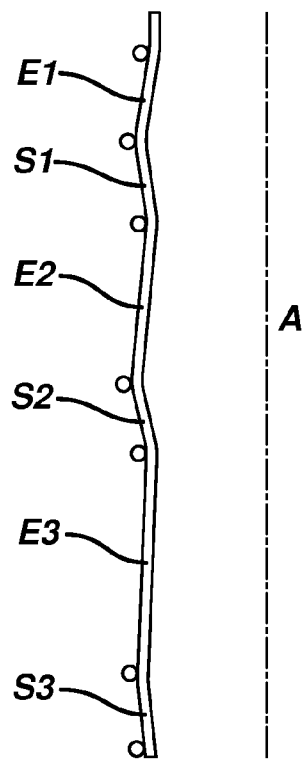
FIG. 6C is a side view of a cannula folding wall of the cannula of FIGS. 6A-6B in an unfolded position.
Figure 6D:
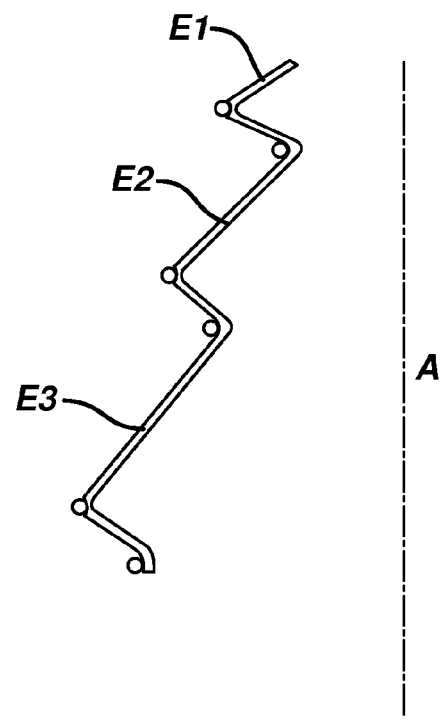
FIG. 6D is a side view of the cannula folding wall of FIG. 6C in a folded position.

In one embodiment, the folding walls 112 include a plurality of segments and, in particular, can include at least one long segment and at least one short segment having a length less than a length of the long segment. In the illustrated embodiment, each folding wall 112 includes three long segments E1, E2, E3 and three short segments S1, S2, S3. As shown, the segments can be defined by living hinges 113 formed in the interior surface 114 and/or exterior surface 116 of the folding walls 112. The living hinges 113 can alternate between being formed in the interior surface 114 of the folding wall 112 and the exterior surface 116. In addition, the long segments can have progressively increasing lengths from the proximal end of the folding walls to the distal end and/or the short segments can each have substantially the same length. For example, in FIG. 6B, all three short segments S1, S2, S3 have the same length L. The long segments E1, E2, E3, on the other hand, have progressively increasing lengths such that the length L3 of the distal-most segment E3 is greater than the length L2 of the intermediate segment E2, which is in turn greater than the length L1 of the proximal-most segment E1. Forming the long segments with progressively increasing lengths from the proximal end to the distal end of the folding walls allows the folding walls to take an angled orientation when folded to define a substantially conical opening. For example, FIG. 6C shows a folding wall in its unfolded state wherein each of the segments S1, S2, S3, E1, E2, E3 are substantially aligned parallel to a longitudinal axis A of the cannula. FIG. 6D illustrates the same folding wall after having been folded at each living hinge. As shown, the folded wall extends at an angle from the axis A.

The seal housing 30, housing 12, and cannula folding walls 112 can be formed from a variety of materials known in the art, including but not limited to various polymers, including polycarbonates and polyetheretherketone (PEEK), metals such as titanium or stainless steel, composites such as carbon-fiber reinforced PEEK, various ceramic materials, and/or any combination thereof. These structures can also be formed of various semi-rigid/flexible materials, including polyurethanes such as Pellethane (available from The Dow Chemical Company of Midland, Mich., USA), thermoplastic elastomers such as Santoprene (available from ExxonMobil Chemical of Houston, Tex., USA), polyisoprene elastomers, medium to high durometer silicone elastomers, and/or any combination thereof. A person having ordinary skill in the art will recognize that any other suitable material, such as fabrics, foams, plastics, and/or metals, can be used to form the structures and devices disclosed herein and that each of the structures and devices can be made from the same materials or from different materials or from any combination of materials. The cannula sheath 106 can be formed from a variety of materials known in the art, including for example various plastics, silicone, polyisoprene, other elastomers or rubbers, and/or any combination thereof. The material or materials chosen for the cannula sheath 106 can have a combination of optimal attributes such as flexibility, strength, durability, breathability, microbial resistance, etc.

As noted above, the access device 10 can also include an actuator configured to move the cannula between the insertion configuration and the expanded configuration. The actuator can include a variety of different mechanisms for effecting movement of the cannula.

In one embodiment, as shown for example in FIG. 2, the actuator includes at least one cable 15 extending distally from the housing 12 to the distal end 22 of the cannula 14, where it is attached thereto. The cables 15 can be attached to the distal end 22 of the cannula 14 using any suitable method known in the art, for example by threading the cables 15 through one or more apertures formed in the cannula 14 until an enlarged head or knot at the distal end of the cable 15 engages an outer surface of the cannula 14 and prevents further threading of the cable therethrough. The proximal end of the cables 15 can extend proximally through the apertures 102 in the base portion 80 of the housing 12 and into the apertures 90 formed in the top portion 82 of the housing 12. The cables can be fixedly attached within the top portion apertures 90 and slidably disposed through the base portion apertures 102. An annular recess 118 can be formed in the proximal surface 98 of the base portion 80 and can be sized to accommodate a length of the cables 15, as shown for example in FIG. 5E.

In use, as shown in FIG. 2, rotation of the housing top portion 82, to which the cables 15 are fixedly attached, with respect to the housing base portion 80 is effective to selectively tension the cables 15. For example, when the base portion 80 is abutted against and fixed to the tissue wall 16, and the top portion 82 is rotated with respect thereto, the cables 15 are translated proximally through the base portion apertures 102. As the top portion 82 is rotated, the top portion apertures 90 become radially offset from the base portion apertures 102, causing the cables 15 to bend approximately 90 degrees in two places at the junction between the base portion 80 and the top portion 82 and to be taken up in and wound around the annular recess 118. The proximal translation of the cables 15 pulls the folding walls 112 of the cannula 14 into a folded position, which in turn deforms the cannula sheath 106 and the surrounding incision outward into a substantially conical shape. The top portion 82 can be rotated until the male tabs 92 formed on the distal surface 88 thereof engage and lock with the female slots 100 formed on the proximal surface 96 of the base portion 80. The locking engagement between the tabs 92 and the slots 100 prevents rotation of the top portion 82 with respect to the base portion 80 in either direction and thus locks the cannula 14 in the expanded, substantially conical shape. The cannula 14 can be expanded before, during, or after a seal housing 30 is attached to the housing 12 and, as noted above, the seal housing 30 can optionally be integrally formed with the housing 12.

As illustrated for example in FIG. 1, when the tabs 92 are subsequently disengaged from the slots 100, the resilient properties of the tissue wall incision can force the folding walls 112 of the cannula 14 back towards a substantially cylindrical insertion configuration. This can in turn draw the cables 15 distally through the base portion apertures 102 and rotate the top portion 80 until the top portion apertures 90 are substantially aligned with the base portion apertures 102 and the cables 15 are substantially straight.

Figure 7B:
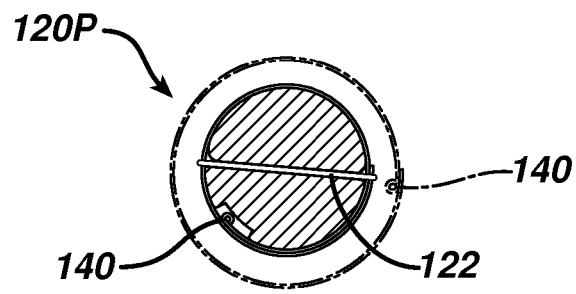
FIG. 7B is cross-sectional top view of one embodiment of a biasing element, one embodiment of a retaining element, and the obturator of FIG. 7A.

In another exemplary embodiment, shown for example in FIGS. 7A-7E, the actuator can include a plurality of biasing elements instead of, or in addition to, the cables described above. FIG. 7A shows the cannula 14' of an access device 10' inserted into a tissue wall 16' such that the housing 12' of the access device 10' rests against an outer surface of the tissue wall 16'. As shown, the cannula 14' is inserted in a first insertion configuration in which it has a substantially cylindrical shape. One or more biasing elements 120 can be disposed within the inner lumen of the cannula 14' and can be biased to expand radially, thereby forcing the cannula 14' into the expanded, conical configuration described above. In the illustrated embodiment, the biasing elements 120 are in the form of coiled springs. One or more retaining elements 122 coupled to the biasing elements 120 can also be provided. The retaining elements 122 can be configured to maintain the biasing elements in a radially contracted position (i.e., a reduced diameter configuration). In use, releasing the retaining elements 122 can allow the biasing elements to expand radially against the inner surface 114 of the cannula 14'.

An obturator 124 configured for releasing the retaining elements 122 can also be provided. The obturator 124 can have a variety of configurations, but in the illustrated embodiment it is in the form of an elongated tubular body 126 with a handle 128 formed on a proximal end thereof. An elongate, diametrical slot 130 and/or a clearance groove 132 can be formed in a distal portion of the obturator body 126. The diametrical slot 130 can extend all the way through the obturator body 126, such that the distal portion is separated into two opposed arms 134, 136. At least one edge 138 of at least one of the opposed arms 134, 136 can be sharpened, serrated, and/or otherwise configured to sever the retaining elements 122 upon application of sufficient force.

Figure 7C:
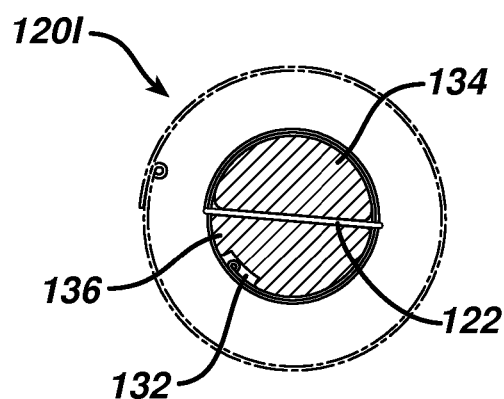
FIG. 7C is cross-sectional top view of one embodiment of a biasing element having an expanded diameter larger than that of the biasing element of FIG. 7B.
Figure 7D:
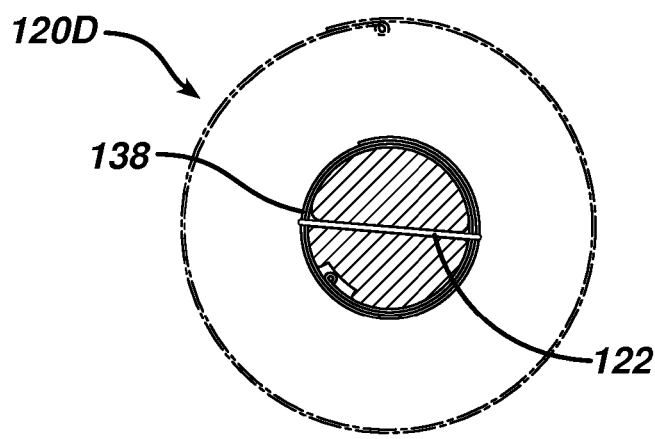
FIG. 7D is cross-sectional top view of one embodiment of a biasing element having an expanded diameter larger than that of the biasing element of FIG. 7C.

In use, the obturator body 126 can be inserted through the working channel of the access device 10'. The obturator handle 128 can remain outside of the access device 10', acting as a stop against the housing 12' to prevent over-insertion of the obturator 124 and to provide a gripping point for a user. When inserted, the opposed arms 134, 136 straddle the retaining elements 122 disposed within the cannula 14', such that the retaining elements are disposed within the diametrical slot 130 in the obturator. Once the access device 10' has been placed through the tissue wall with the cannula 14' in a substantially cylindrical insertion configuration and the obturator 124 inserted therethrough, the obturator 124 can be rotated with respect to the access device 10' such that the sharpened edge 138 of the opposed arm(s) 134, 136 severs one or more of the retaining elements 122. After the retaining elements 122 are severed, the biasing elements 120 to which they are attached become free to expand radially against the interior surface 116 of the cannula 14', forcing the cannula towards a substantially conical expanded configuration. As illustrated, the biasing elements 120 can be substantially aligned with the living hinges 113 formed in the folding walls 112 of the cannula 14' to achieve maximal expansion.

Where multiple biasing elements 120 are provided, they can be sized to have progressively increasing diameters in their unrestrained states that correspond to the progressively increasing lengths of the cannula's folding wall segments. In the embodiment of FIG. 7A-7E, three biasing elements 120 are disposed within the cannula 14'. FIG. 7B shows the proximal-most biasing element 120P, FIG. 7C shows the intermediate biasing element 120I, and FIG. 7D shows the distal-most biasing element 120D. The biasing elements 120 in each of these figures is shown from above being maintained in a restrained diameter by a retaining element 122. The unrestrained diameter of the biasing elements 120 is shown in phantom.

Figure 7E:
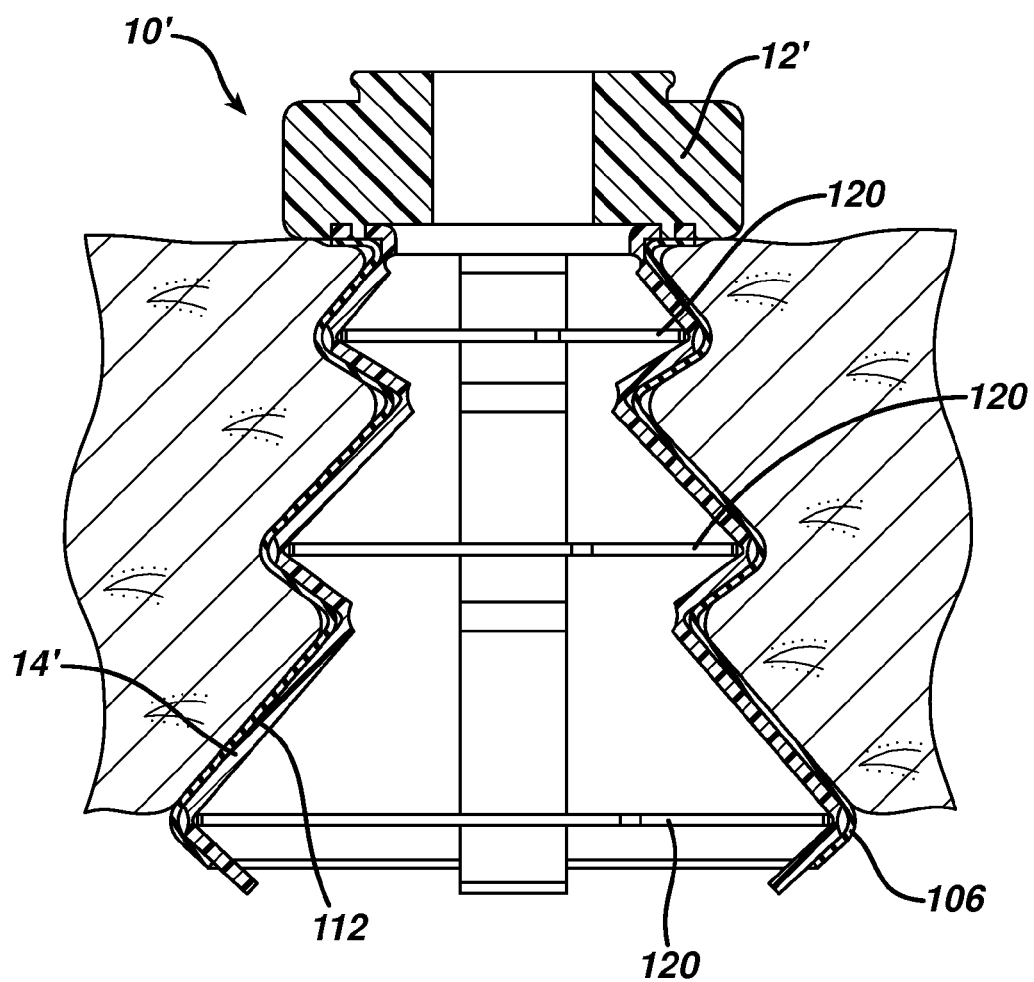
FIG. 7E is a cross-sectional side view of the access device of FIG. 7A, with the cannula shown in an expanded configuration.

As illustrated, the biasing elements 120P, 120I, and 120D have progressively increasing diameters in their unrestrained states such that the diameter of the distal-most biasing element 120D is greater than the diameter of the intermediate biasing element 120I, which is in turn greater than the diameter of the proximal-most biasing element 120P. In their restrained states, each of the biasing elements 120 have substantially the same diameter. As shown in FIG. 7E, this progressive sizing of the biasing elements 120 in their unrestrained states, combined with the progressive sizing of the folding wall segments of the cannula 14', facilitates deformation of the cannula 14' to a substantially conical shape.

In some instances it can be desirable to re-wind the biasing elements 120 after the retaining elements 122 have been severed, for example when it is necessary to remove the access device 10' from the tissue wall. To that end, the biasing elements 120 can further include a grasping feature 140 formed at a terminal end thereof to facilitate re-winding. As shown in FIGS. 7B-7D, the grasping feature 140 can be in the form of a small loop formed at or near a terminal end of the coiled spring biasing element 120. A surgical grasping tool or other suitable device can be inserted through the working channel of the access device 10' to grip the grasping feature 140 and re-wind the biasing element 120. The clearance groove 132 formed in the obturator body 126 can be sized to accommodate the grasping feature 140, as shown for example in FIGS. 7B-7D.

Figure 7F:
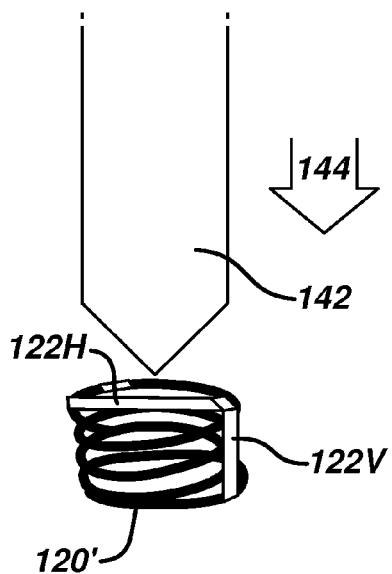
FIG. 7F is a perspective view of an obturator and one embodiment of a biasing element having a horizontal retaining element and a vertical retaining element attached thereto.
Figure 7G:
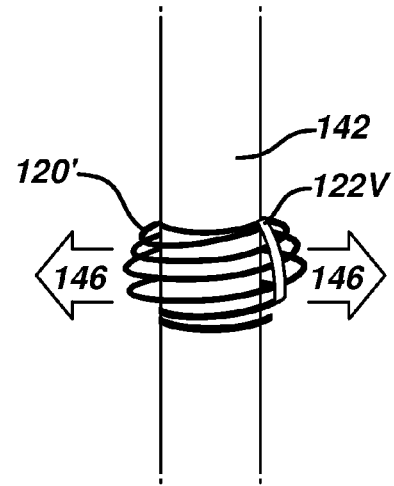
FIG. 7G is a perspective view of the biasing element of FIG. 7F after the horizontal retaining element is severed.
Figure 7H:
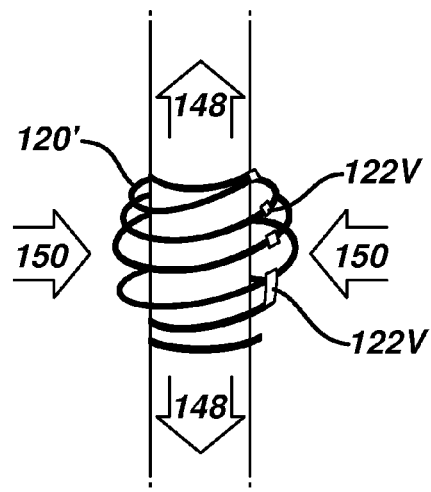
FIG. 7H is a perspective view of the biasing element of FIGS. 7F and 7G after the vertical retaining element is severed.

In another embodiment, a solid-tipped obturator, e.g., an obturator without a diametrical slot, can be provided that is configured to sever the retaining elements as the obturator is advanced distally into the access device. In addition, the retaining elements can include both horizontal retaining elements, which can restrain a biasing element from radial expansion, and vertical retaining elements, which can restrain a biasing element from longitudinal expansion. FIGS. 7F-7H illustrate one embodiment of such a configuration. In FIG. 7F, a solid-tipped obturator 142 is shown advancing distally into a biasing element 120'. The biasing element 120' includes a horizontal retaining element 122H and a vertical retaining element 122V. When the obturator 142 is advanced in the direction of the arrow 144, it can sever the horizontal retaining element 122H attached to the biasing element 120'. FIG. 7G shows the obturator 142 having been advanced through the biasing element 120', and having severed the horizontal retaining element 122H, such that the biasing element 120' is allowed to expand radially in the direction of arrows 146 and thereby urge a cannula (not shown) towards an expanded configuration. The vertical retaining element 122V is not severed by the obturator 142.

When it later becomes desirable to return the cannula to an insertion configuration, a cutting tool can be inserted through the working channel of the access device to sever the vertical retaining element 122V. FIG. 7H illustrates the biasing element 120' after the vertical retaining element 122V has been severed. As shown, the biasing element 120' is allowed to expand longitudinally in the direction of arrows 148. This longitudinal expansion causes a commensurate radial contraction in the direction of arrows 150, allowing the cannula (not shown) to return to a substantially cylindrical insertion configuration.

In another exemplary embodiment, shown for example in FIGS. 8A-8B, the actuator can be in the form of one or more bimodal rings 152. A bimodal ring 152 in accordance with this embodiment has a first configuration (shown in FIG. 8A) in which it has a convex interior surface 154 and a maximum diameter D1. The bimodal ring 152 also has a second configuration (shown in FIG. 8B) in which it has a concave interior surface 156 and a maximum diameter D2, which is greater than the diameter D1. When an obturator 158 is inserted through a bimodal ring 152 in the first configuration, the convex interior surface 154 can be urged radially outward by the obturator 158 until the bimodal ring "snaps" into the second configuration. The one or more bimodal rings 152 can be progressively sized such that the radial expansion that occurs when the rings 152 are transitioned from the first configuration to the second configuration is effective to deform a cannula in which the rings are disposed into a substantially conical shape. In an exemplary embodiment, the rings are formed from a flexible, semi-resilient material, such as various plastics, polymers, rubbers, and/or metals known in the art.

Figure 9A:
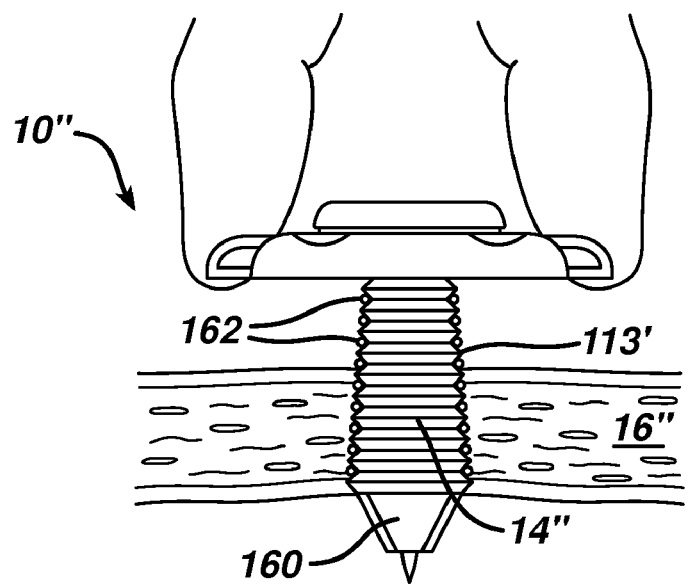
FIG. 9A is a side view of another embodiment of an access device having a cannula in an insertion configuration with an obturator inserted therethrough.

In yet another embodiment of an access device, the actuator can include a plurality of springs disposed circumferentially around the cannula and biased to apply an inward force to the cannula, biasing the cannula to the expanded configuration. An obturator can be provided in such embodiments that is configured such that insertion of the obturator into the cannula is effective to radially expand the plurality of springs, thereby moving the cannula to an insertion configuration. When the obturator is removed, the springs are allowed to radially contract, moving the cannula to the expanded configuration. FIG. 9A illustrates an access device 10" and an obturator 160 inserted therethrough being advanced distally through a tissue wall 16". A plurality of springs 162 are disposed circumferentially around the cannula 14". The cannula 14" can be similar or identical to the cannulas 14, 14' described above, and can thus have one or more folding walls 112' that include a plurality of long segments 164 and a plurality of short segments 166. The long segments 164 can have progressively increasing lengths from the proximal end of the cannula 14" to the distal end, while the short segments can have substantially the same lengths. The plurality of springs 162 can be substantially aligned with the living hinges 113' formed on the interior surface of the cannula 14", which, together with the living hinges 113' formed on the exterior surface of the cannula 14", define the plurality of segments in the folding wall or walls 112'.

Figure 9B:
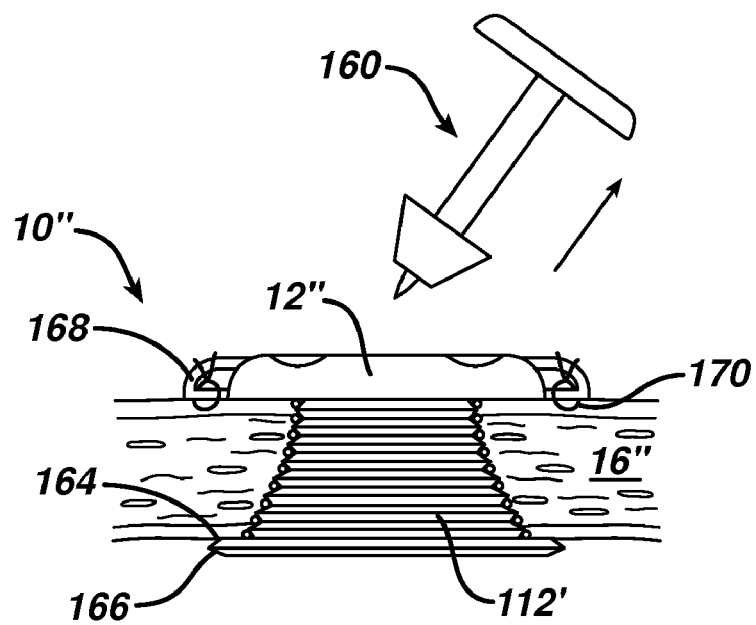
FIG. 9B is a side view of the access device of FIG. 9A with the obturator removed to allow the cannula to move to an expanded configuration.

As shown in FIG. 9B, when the obturator 160 is removed from the access device 10", the plurality of springs 162 are allowed to radially contract, collapsing the folding walls 112' slightly at each interior surface living hinge. The alignment of the springs 162 with the interior surface livings hinges causes the short segments 166 to angle inwardly towards a longitudinal axis of the cannula 14', which in turn causes the long segments 164 to angle outwardly away from the longitudinal axis. The progressively increasing lengths of the long segments 164, in combination with this outward angulation, results in the cannula 14" taking a substantially conical shape, as shown. The housing 12" of this embodiment, as well as the housings of all other embodiments discussed herein, can optionally include one or more slots, tabs, and/or apertures 168 for receiving tie down sutures 170 or any other suitable device for securing the housing 12" to the tissue wall 16".

Figure 10A:
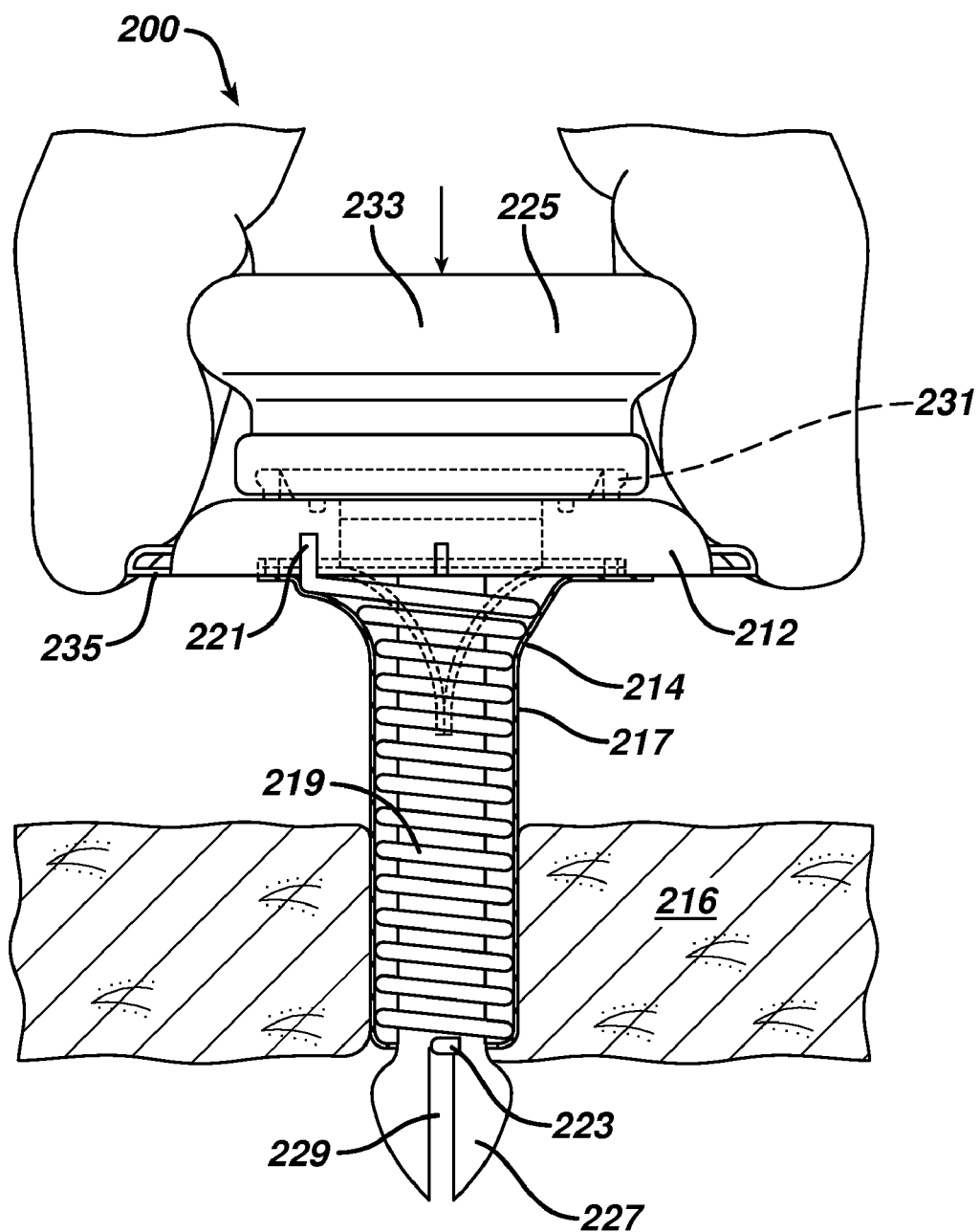
FIG. 10A is a cross-sectional side view of another embodiment of an access device having a coil spring disposed within a cannula and an obturator inserted therethrough, shown with the cannula in an insertion configuration.

FIG. 10A illustrates another exemplary embodiment of an access device 200. The access device generally includes a housing 212 and a cannula 214 extending therefrom. The access device 200 can also include one or more seals, as explained above with respect to FIG. 1. The seals can be disposed in any portion of the access device 200, including in a separate seal housing (not shown). The housing 212, cannula 214, and seal housing can have substantially the same features as the housings 12, cannulas 14, and seal housings 30 described above. In the illustrated embodiment, the cannula 214 includes a flexible, expandable sheath 217. The cannula 214 also includes a coil spring 219 having a proximal end 221 that is coupled to the housing 212 and a distal end 223. The housing 212 can include an aperture configured to receive the proximal end 221 of the spring 219. The distal end 223 of the spring 219 can be configured to rotate relative to the housing 212 such that the coil spring 219 winds or unwinds to adjust a diameter of the cannula 214. The coil spring 219 can be shaped such that, when unwound, it has a generally conical shape and when wound, it has a generally cylindrical shape. For example, the coil spring 219 can have a plurality of coils extending radially around a longitudinal axis of the cannula 214 and can be biased to a configuration in which the diameter of each individual coil increases progressively from the proximal-most coil to the distal-most coil. When configured in such a way, the coil spring 219 can be wound to allow the cannula 214 to move to an insertion configuration in which it has a substantially constant outer diameter and can be unwound to stretch the cannula 214 to an expanded configuration in which the diameter of the cannula 214 increases from the proximal end of the cannula to the distal end of the cannula. An obturator 225 can also be provided that has a distal end 227 configured to engage the distal end 223 of the coil spring 219 such that rotation of the obturator is effective to rotate the distal end 223 of the coil spring 219 relative to the housing 212 and thus to wind or unwind the coil spring 219.

As shown in FIG. 10A, the coil spring 219 can be wound such that the cannula 214 has a substantially constant outer diameter. An obturator can be inserted through the access device 210 to maintain the spring 219 in a wound state. A diametrical slot 229 formed in the distal end 227 of the obturator 225 can receive and engage the distal end 223 of the coil spring 219, which can extend at least partially across a longitudinal axis of the cannula, as shown for example in FIG. 10B. One or more snap connections 231 can be included to lock the obturator handle 233 to the housing 212 such that it cannot rotate with respect thereto. Locking the obturator with respect to the housing 212 can prevent the coil spring 219 from unwinding. Once the access device 210 is inserted through the tissue wall 216, one or more sutures or other suitable tie-down mechanisms can be coupled to one or more anchor slots 235 formed in the housing 212 to secure the access device 210 to the tissue wall 216.

As shown in FIG. 10C, the snap connections 231 can be released to allow the obturator 225 to rotate with respect to the housing 212. The biased nature of the coil spring 219 can cause it to unwind, thereby rotating the obturator 225. A force can be applied by the surgeon to the obturator handle 233 to "brake" or otherwise modulate the rotation speed of the obturator 233 and therefore the unwinding speed of the coil spring 219. One or more sutures 237 can be threaded through the anchor slots 235 to prevent the housing 212 from rotating with respect to the tissue wall 216 due to the force of the unwinding coil spring 219 when the snap connections 231 are released. Once the coil spring 219 is unwound, the cannula 214 is deformed to form a substantially conical opening through the tissue wall 216. The obturator 225 can then be withdrawn proximally from the access device 210 to allow attachment of a seal housing or to allow insertion of other surgical tools through the device 210.

As shown in FIGS. 10C-10D, a zero-closure seal 242, such as a duckbill seal as described above, can be provided in the cannula 214 and/or the housing 212. A person skilled in the art will appreciate that the seal 242 allows the obturator 225 to be withdrawn from the device 210 without compromising the insufflation of the body cavity underlying the tissue wall 216. In other words, the seal 242 can maintain insufflation pressure after the obturator 225 is removed but before a seal housing 30 is attached to the housing 212.

Figure 10E:
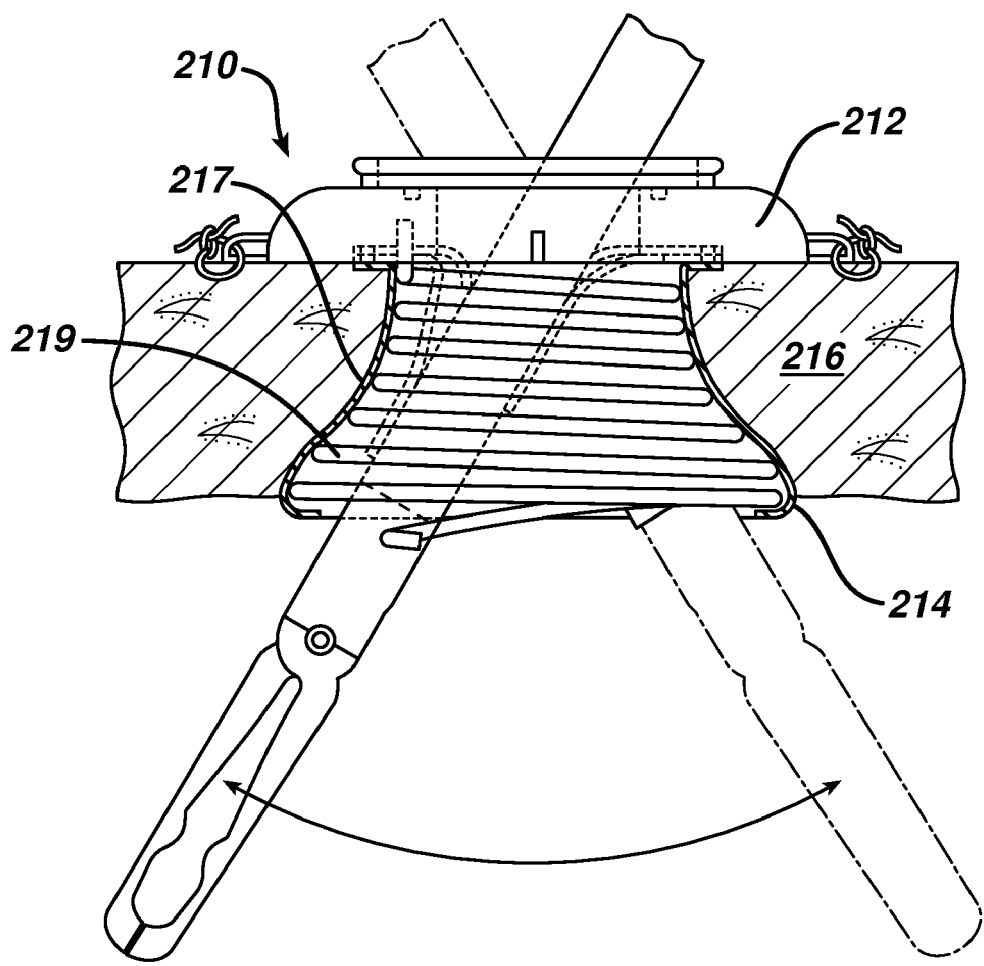
FIG. 10E is a cross-sectional view of a surgical tool inserted through the access device of FIG. 10A and angulated to a first position, with a phantom view of the surgical tool angulated to a second position.

The conical opening formed by the access device 210 when the coil spring 219 is unwound can advantageously allow surgical instruments inserted through the device to be angulated to a much greater degree than in a typical cylindrical cannula device, as depicted in FIG. 10E. The conical shape also aids in retention of the access device 210, as it can prevent unintended proximal translation of the device with respect to the tissue wall 216. In addition, the biased nature of the coil spring 219 can force the cannula sheath 217 against the tissue wall 216 to increase the integrity of a seal formed therebetween.

Figure 10F:
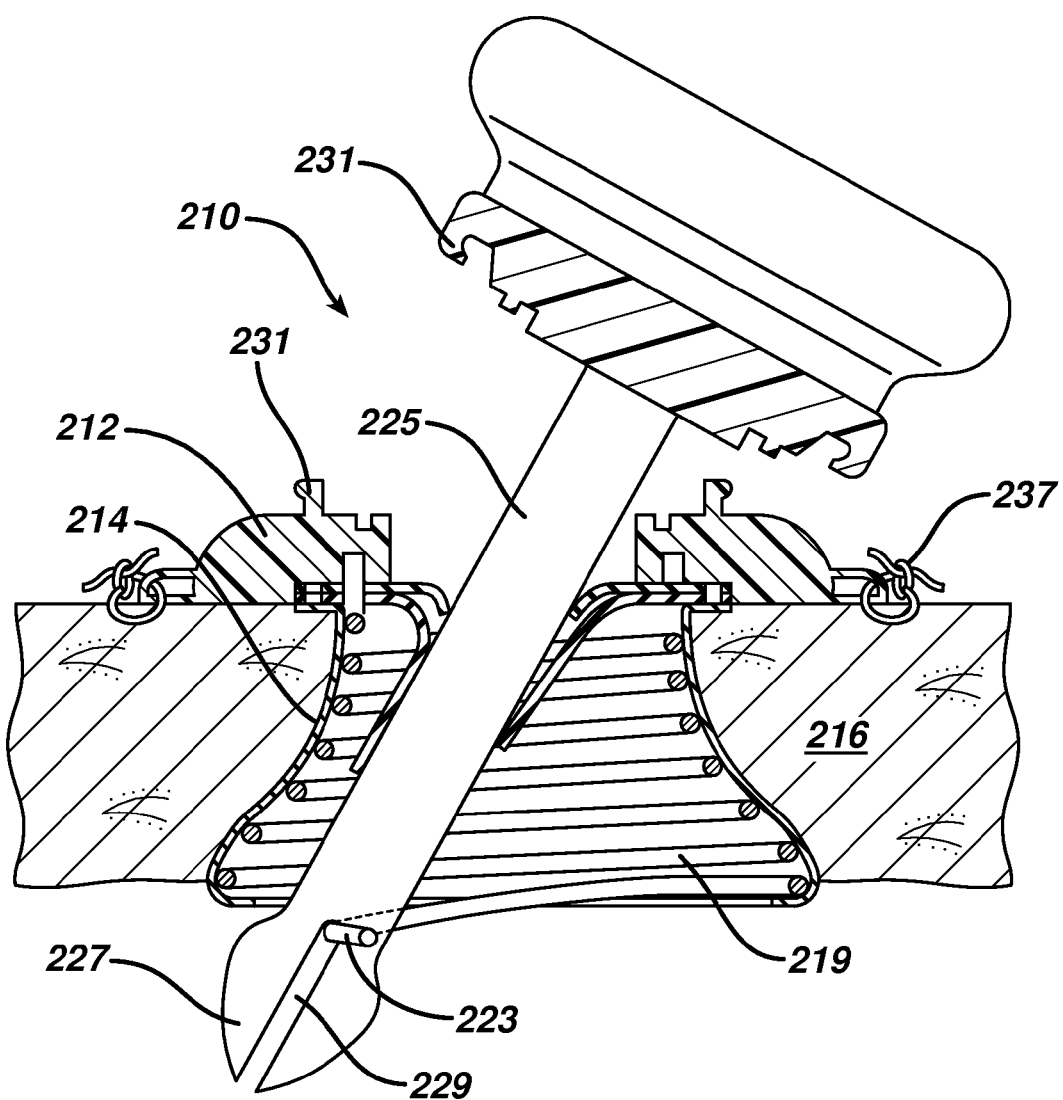
FIG. 10F is a cross-sectional view of the access device of FIG. 10A with the obturator inserted to wind the coil spring.

When it is desirable to return the cannula 214 to the insertion configuration, such as when a surgical procedure has been completed, the obturator 225 can be used to re-wind the coil spring 219, as shown for example in FIG. 10F. The obturator 225 can be inserted through the housing 212 at a slight angle such that the diametrical slot 229 formed in the distal end 227 thereof can engage the distal end 223 of the coil spring 219. Once engaged, the obturator 225 can be rotated with respect to the housing 212 to wind the coil spring 219 and return the cannula 214 to the insertion configuration. Again, the sutures 237 can prevent the housing 212 from rotating as the obturator 225 is rotated to wind the spring 219. After the coil spring 219 is sufficiently wound, the snap connections 231 can be engaged to lock the obturator 225 with respect to the housing 212 and prevent rotation therebetween. The access device 210 can then be withdrawn proximally from the tissue wall 216.

In use, the devices disclosed herein can enable a user to access a surgical site and to conduct one or more surgical procedures. Although various methods of using surgical access devices are discussed herein with respect to particular embodiments of surgical access devices and their related components, a person skilled in the art will recognize that, to the extent that the features of the various surgical access devices disclosed herein are interchangeable between embodiments, many of the steps of the methods are likewise interchangeable.

Generally, a surgical site can be accessed by inserting a cannula of the surgical access device through a tissue wall. For example, in one embodiment an incision can be formed through the abdominal wall of a patient and the cannula can be inserted therethrough in an insertion configuration. The cannula can then be manipulated in a variety of ways to take on an expanded configuration and thereby create a conical opening through the tissue. In one embodiment, the cannula can have folding walls that can be folded to form the conical shaped opening. For example, in the surgical access device 10 of FIGS. 1-2, the housing top portion 82 can be rotated with respect to the housing base portion 80 to draw the cables 15 proximally and/or apply tension to the cables 15 and thereby fold the folding walls 112 of the cannula 14. The cannula can also be folded using a variety of other techniques, for example by inserting an obturator through the cannula to sever one or more retaining elements to allow one or more biasing elements to expand radially as shown in FIGS. 7A-7E and/or by removing an obturator from the cannula to allow one or more springs to contract radially against an outer surface of the cannula as shown in FIGS. 9A-9B. The conical shaped opening can also be formed by releasing a coil spring disposed within the cannula such that the coil spring radially expands and causes the cannula to radially expand as shown in FIGS. 10A-10F. Either before or after forming the conical opening through tissue, one or more sutures or other tie-down features known in the art can be used to secure the surgical access device. The seal housing can be attached to the device either prior to or after insertion of the cannula through the tissue wall. Insufflation fluid can be applied to the surgical site via an insufflation port, as shown for example in FIG. 4. One or more instruments can then be inserted through and/or removed from the surgical access device to perform any number of procedures. When the procedure is complete, the cannula can be moved to the insertion configuration and then removed from the tissue wall.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An adjustable access device, comprising:
  a housing having a cannula extending distally therefrom, the housing and the cannula defining a working channel extending therethrough for receiving instruments; and at least one seal element disposed within the working channel and configured to form at least one of a seal around an instrument disposed through the working channel and a seal across the working channel when no instrument is disposed therethrough;

wherein the cannula is movable between an insertion configuration in which the cannula has a substantially constant outer diameter and an opening defining a distal end of the working channel has a first diameter, and an expanded configuration in which the outer diameter of the cannula increases from a proximal end of the cannula to a distal end of the cannula and the opening has a second diameter that is greater than the first diameter, the cannula being folded in the expanded configuration and unfolded in the insertion configuration.

2. The device of claim 1, wherein the cannula comprises a flexible outer sheath having a plurality of folding walls disposed therein, each folding wall comprising a plurality of segments.

3. The device of claim 2, wherein the plurality of segments comprise a plurality of long segments separated from each other by at least one short segment.

4. The device of claim 3, wherein the segments are defined by a plurality of living hinges formed in the folding walls.

5. The device of claim 4, wherein the living hinges alternate between being formed in an interior surface of the folding walls and being formed in an exterior surface of the folding walls.

6. The device of claim 5, wherein the plurality of long segments have progressively increasing lengths from the proximal end of the folding walls to the distal end of the folding walls.

7. The device of claim 6, wherein each of the short segments have substantially the same length.

8. The device of claim 1, further comprising an actuator coupled between the housing and the cannula and configured to move the cannula between the insertion configuration and the expanded configuration.

9. The device of claim 8, wherein the actuator comprises at least one cable extending distally from the housing to the distal end of the cannula.

10. The device of claim 9, wherein the housing includes a rotatable member coupled to the at least one cable and configured to rotate to selectively tension the at least one cable.

11. The device of claim 1, further comprising at least one biasing element disposed within the cannula and configured to bias the cannula towards the expanded configuration.

12. The device of claim 11, further comprising a horizontal retaining element coupled to the biasing element such that the cannula is maintained in the insertion configuration.

13. The device of claim 12, further comprising a vertical retaining element coupled to the biasing element such that the cannula is maintained in the expanded configuration.

14. An adjustable access device, comprising:
a housing having a cannula extending distally therefrom, the housing and the cannula defining a working channel extending therethrough for receiving instruments; and
at least one seal element disposed within the working channel and configured to form at least one of a seal around an instrument disposed through the working channel and a seal across the working channel when no instrument is disposed therethrough;
wherein the cannula has an insertion configuration with a substantially constant outer diameter between a proximal end and a distal end, and an expanded configuration wherein the diameter increases from the proximal end of the cannula to the distal end of the cannula, the cannula being folded in the expanded configuration and unfolded in the insertion configuration;
wherein the cannula comprises a flexible outer sheath having a plurality of folding walls disposed therein, each folding wall comprising a plurality of segments defined by a plurality of living hinges that alternate between being formed in an interior surface of the folding wall and being formed in an exterior surface of the folding wall; and
wherein the plurality of segments comprise a plurality of long segments separated from each other by at least one short segment, the plurality of long segments having progressively increasing lengths from a proximal end of the folding walls to a distal end of the folding walls.

15. The device of claim 14, wherein each of the short segments have substantially the same length.

* * * * *